(12) United States Patent
Tajima et al.

(10) Patent No.: US 7,718,119 B2
(45) Date of Patent: May 18, 2010

(54) METHOD AND APPARATUS FOR GENERATING SMELL

(76) Inventors: Yukinobu Tajima, 6-22, Komaba 2-chome, Saitama-shi, Saitama 336-0908 (JP); Hideki Tanemura, 2-12, Nijukki-machi, Shinjuku-ku, Tokyo 162-0855 (JP); Naoki Urushihata, 5-2-15-203, Nakayama Satsukidai, Takarazuka-shi, Hyogo 665-0871 (JP)

( * ) Notice: Subject to any disclaimer, the term of this patent is extended or adjusted under 35 U.S.C. 154(b) by 787 days.

(21) Appl. No.: 10/275,820

(22) PCT Filed: May 28, 2001

(86) PCT No.: PCT/JP01/04444

§ 371 (c)(1),
(2), (4) Date: Nov. 12, 2002

(87) PCT Pub. No.: WO01/89590

PCT Pub. Date: Nov. 29, 2001

(65) Prior Publication Data

US 2004/0101447 A1 May 27, 2004

(30) Foreign Application Priority Data

May 26, 2000 (JP) .............................. 2000-157248

(51) Int. Cl.
*A61L 2/00* (2006.01)
*A61L 2/04* (2006.01)
*A61L 9/00* (2006.01)
*G03B 21/32* (2006.01)

(52) U.S. Cl. .................. 422/5; 422/1; 422/20; 422/22; 422/39; 422/120; 422/123; 422/124; 422/125; 422/305; 422/307; 239/305; 239/34; 239/53; 239/690; 239/303; 222/146.5; 352/85

(58) Field of Classification Search .................... 422/1, 422/5, 20, 39, 120, 125, 123, 124, 305, 307; 239/305, 34, 53, 690, 303; 222/143.5; 352/85
See application file for complete search history.

(56) References Cited

U.S. PATENT DOCUMENTS 5,011,632 A * 4/1991 Yano et al. .................... 261/81

(Continued)

FOREIGN PATENT DOCUMENTS

EP 0 831 384 A 3/1998

(Continued)

*Primary Examiner*—William H Beisner
*Assistant Examiner*—Nathan A Bowers
(74) *Attorney, Agent, or Firm*—Oliff & Berridge, PLC

(57) ABSTRACT

An apparatus and method for generating a desired smell by processing smell information through a combination of a computer system and a perfume generating means. In order to generate a desired smell under control of a computer, preset perfume information concerning a smell classification table, kinds of preset perfume corresponding to the items of smell in the smell classification table, the amount of smell to be generated and the variation with time of the amount is registered, the item of a specific smell is selected from the smell classification table, and relevant pieces of the preset perfume information corresponding to the item of the specific smell is extracted. A deodorant may be combined or various smells may be combined with an image.

20 Claims, 12 Drawing Sheets

U.S. PATENT DOCUMENTS

| | | | |
|---|---|---|---|
| 5,023,020 A * | 6/1991 | Machida et al. | 261/18.1 |
| 5,724,256 A * | 3/1998 | Lee et al. | 700/285 |
| 5,949,522 A | 9/1999 | Manne | |
| 2001/0001303 A1* | 5/2001 | Ohsuga et al. | 482/5 |
| 2008/0215037 A1* | 9/2008 | Petrakis | 604/890.1 |

FOREIGN PATENT DOCUMENTS

| | | |
|---|---|---|
| JP | 06127575 A * | 5/1994 |
| JP | A 6-142172 | 5/1994 |
| JP | 09010290 A * | 1/1997 |
| JP | 10-146385 A | 6/1998 |
| WO | WO 99/38102 | 7/1999 |
| WO | WO 0015269 * | 3/2000 |
| WO | WO 01/07094 A1 | 2/2001 |

* cited by examiner (a)

(b)

(c)

(a)

(b)

METHOD AND APPARATUS FOR GENERATING SMELL

TECHNICAL FIELD

The present invention relates to a novel apparatus and method for generating a smell by combining a computer system and perfume generating means.

BACKGROUND ART

Visual information and acoustic information have been widely supplied or exchanged by combining a computer system with image display means and/or sound generating means.

Under such a situation, Japanese Patent Application Laid-Open Publication No. 10-146385 has disclosed a concept of generating a desired smell by processing smell information by combination of the computer system and perfume generating means. However, this proposal does not contain a technical idea on what smell should be generated, and furthermore, if the generation of some kind of a smell is attempted, a smell which befits a given situation needs to be selected.

DISCLOSURE OF THE INVENTION

To solve the above-described problem, the present invention provides a novel smell generating apparatus and smell generation method capable of processing the smell information by combination of the computer system with perfume generating means and capable of generating a desired smell which befits a given scene or situation by using the perfume information registration means and perfume information selecting and extracting means.

According to the first aspect of the present invention, there is provided a smell generating apparatus for generating a desired smell under computer control, characterized by including: (A) a plurality of perfume containing members; (B) perfume information registration means for registering preset perfume information on a smell classification table and kinds of the preset perfumes corresponding to smell items in the smell classification table, its generation amount and the variation with time of that generation amount; (C) perfume information selecting and extracting means for selecting a predetermined smell item from the smell classification table and extracting the preset perfume information corresponding to the predetermined smell item; (D) smell generation control means for controlling smell generation according to the smell generation program and the perfume information; (E) smell selecting means for selecting a specific perfume containing member from the perfume containing members under control of the smell generation control means; (F) smell generating means for generating a smell from the specific perfume containing member based on the smell selecting means; (G) smell generation program storage means for storing the smell generation program; and (H) image display means.

According to the second aspect of the present invention, there is provided a smell generating apparatus for generating a desired smell under computer control, characterized by including: (A) a plurality of perfume containing members; (B1) perfume information registration means for registering preset perfume information on a smell classification table and kinds of the preset perfumes corresponding to smell items in the smell classification table, its generation amount and the variation with time of that generation amount, and perfume information (simulation) changed after that; (C1) perfume information selecting and extracting means for selecting a predetermined smell item from the smell classification table and extracting the preset perfume information corresponding to the predetermined smell item or a changed perfume information; (D1) smell generation control means for carrying out simulation control on smell generation according to the smell generation program, and either of the preset perfume information and the changed perfume information; (E) smell selecting means for selecting a specific perfume containing member from the perfume containing members under control of the smell generation control means; (F) smell generating means for generating a smell from the specific perfume containing member based on the smell selecting means; (G) smell generation program storage means for storing the smell generation program; and (H) image display means.

According to the third aspect of the present invention, there is provided a smell generating apparatus for generating a desired smell under computer control, characterized by including: (A) a plurality of perfume containing members; (P) at least one deodorant container; (B) perfume information registration means for registering preset perfume information on a smell classification table and kinds of the preset perfumes corresponding to smell items in the smell classification table, its generation amount and the variation with time of that generation amount; (Q) deodorant information registration means for registering a preset deodorant information on a deodorant classification table, kinds of preset deodorants corresponding to deodorant items in the deodorant classification table, its generation amount and the variation with time of that generation amount; (C2) perfume information selecting and extracting means for selecting a predetermined smell item from the smell classification table and extracting the preset perfume information corresponding to the predetermined smell item; (R) deodorant information extracting means for selecting a predetermined deodorant item from the deodorant classification table and extracting the preset deodorant information corresponding to the predetermined deodorant item; (D) smell generation control means for controlling smell generation according to the smell generation program and the perfume information; (S) deodorant generation control means for controlling generation of deodorant according to the deodorant generation program and the deodorant information; (E) smell selecting means for selecting a specific perfume containing member from the perfume containing members under control of the smell generation control means; (T) deodorant selecting means for selecting a specific deodorant containing member from the deodorant containing members under control of the deodorant generation control means; (F) smell generating means for generating a smell from the specific perfume containing member based on the smell selecting means; (U) deodorant generating means for generating deodorant from the specific deodorant containing member based on the deodorant selecting means; (G) smell generation program storage means for storing the smell generation program; (V) deodorant generation program storage means for storing the deodorant generation program; and (H) image display means.

According to the fourth aspect of the present invention, there is provided a smell generating apparatus for generating a desired smell under computer control, characterized by including: (A) a plurality of perfume containing members; (P) at least one deodorant container; (B) perfume information registration means for registering preset perfume information on a smell classification table and kinds of the preset perfumes corresponding to smell items in the smell classification table, its generation amount and the variation with time of that generation amount, and perfume information (simulation) changed after that; (Q1) deodorant information registration means for registering preset deodorant information on a deodorant classification table and kinds of the preset deodorants corresponding to deodorant items in the deodorant classification table, its generation amount and the variation with time of that generation amount, and deodorant information (simulation) changed after that; (C3) perfume information selecting and extracting means for selecting a predetermined smell item from the smell classification table and extracting the preset perfume information corresponding to the predetermined smell item or changed perfume information; (R1) deodorant information selecting and extracting means for selecting a predetermined deodorant item from the deodorant classification table and extracting the preset deodorant information corresponding to the predetermined deodorant item or changed deodorant information; (D2) smell generation control means for carrying out simulation control on smell generation according to the smell generation program, and either the perfume information or the changed perfume information; (S1) deodorant generation control means for carrying out simulation control on deodorant generation according to the deodorant generation program, and either the preset deodorant information or the changed deodorant information; (E) smell selecting means for selecting a specific perfume containing member from the perfume containing members under control of the smell generation control means; (T) deodorant selecting means for selecting a specific deodorant containing member from the deodorant containing members under control of the deodorant generation control means; (F) smell generating means for generating a smell from the specific perfume containing member based on the smell selecting means; (U) deodorant generating means for generating deodorant from the specific deodorant containing member based on the deodorant selecting means; (G) smell generation program storage means for storing the smell generation program; (V) deodorant generation program storage means for storing the deodorant generation program; and (H) image display means.

According to the fifth aspect of the present invention, there is provided a smell generating apparatus for generating a desired smell under computer control, characterized by including: (A) a plurality of perfume containing members; (P) at least one deodorant containing member; (B) perfume information registration means for registering preset perfume information on a smell classification table and kinds of the preset perfumes corresponding to smell items in the smell classification table, its generation amount and the variation with time of that generation amount; (Q2) deodorant information registration means for registering preset deodorant information on a deodorant classification table and kinds of the preset deodorants corresponding to deodorant items in the deodorant classification table, its generation amount and its generation time; (C) perfume information selecting and extracting means for selecting a predetermined smell item from the smell classification table and extracting the preset perfume information corresponding to the predetermined smell item; (R2) deodorant information extracting means for selecting a predetermined deodorant item from the deodorant classification table and extracting the preset deodorant information corresponding to the predetermined deodorant item; (D) smell generation control means for controlling smell generation according to the smell generation program and the perfume information; (S2) deodorant generation control means for controlling deodorant generation by the deodorant information extracting means corresponding to the smell generation program and the perfume information; (E) smell selecting means for selecting a specific perfume containing member from the perfume containing members under control of the smell generation control means; (T) deodorant selecting means for selecting a specific deodorant containing member from the deodorant containing members under control of the deodorant generation control means; (F) smell generating means for generating a smell from the specific perfume containing member based on the smell selecting means; (U) deodorant generating means for generating deodorant from the specific deodorant containing member based on the deodorant selecting means; (G) smell generation program storage means for storing the smell generation program; and (H) image display means.

According to the sixth aspect of the present invention, there is provided a smell generating apparatus for generating a desired smell under computer control, characterized by including: (A) a plurality of perfume containing members; (P) at least one deodorant containing member; (B1) perfume information registration means for registering preset perfume information on a smell classification table and kinds of the preset perfumes corresponding to smell items in the smell classification table, its generation amount and the variation with time of that generation amount, and perfume information (simulation) changed after that; (Q3) deodorant information registration means for preset registering preset deodorant information on the kinds of deodorants corresponding to the kinds of the perfumes, its generation amount and its generation time and corrected deodorant information corresponding to the perfume information (simulation) changed after that; (C1) perfume information selecting and extracting means for selecting a predetermined smell item from the smell classification table and extracting the preset perfume information corresponding to the predetermined smell item and changed perfume information; (R3) deodorant information extracting means for extracting the preset deodorant information corresponding to the perfume information selecting and extracting means; (D2) smell generation control means for carrying out simulation control on smell generation according to the smell generation program and either of the preset perfume information or the changed perfume information; (S3) deodorant generation control means for controlling deodorant generation by the deodorant information extracting means corresponding to the smell generation program and the perfume information; (E) smell selecting means for selecting a specific perfume containing member from the perfume containing members under control of the smell generation control means; (T) deodorant selecting means for selecting a specific deodorant containing member from the deodorant containing members under control of the deodorant generation control means; (F) smell generating means for generating a smell from the specific perfume containing member based on the smell selecting means; (U) deodorant generating means for generating deodorant from the specific deodorant containing member based on the deodorant selecting means; (G) smell generation program storage means for storing the smell generation program; and (H) image display means.

According to the seventh aspect of the present invention, there is provided a smell generating apparatus, in which each deodorant containing member is selected independently from a group consisting of containers containing deodorant and members coated with or impregnated with deodorant.

According to the eighth aspect of the present invention, there is provided a smell generating apparatus, in which each perfume containing member is selected independently from a group consisting of containers containing perfume and members coated with or impregnated with perfume.

According to the ninth aspect of the present invention, there is provided a smell generating apparatus, in which the member coated with or impregnated with perfume or deodorant is made of porous ceramic or porous metal.

According to the tenth aspect of the present invention, there is provided a smell generating apparatus, in which the smell generating means is at least one selected from a group consisting of wind, heat, pressure, light and vibration.

According to the eleventh aspect of the present invention, there is provided a smell generating apparatus, in which the member coated with or impregnated with perfume or deodorant is used as a rotating body of a fan for generating wind.

According to the twelfth aspect of the present invention, there is provided a smell generating apparatus, provided with image reproducing means and/or sound generating means.

According to the thirteenth aspect of the present invention, there is provided a smell generating apparatus provided with communication means.

According to the fourteenth aspect of the present invention, there is provided a smell generating method for generating a desired smell under a control by computer, characterized by including steps of: preliminarily registering a smell classification table and perfume information composed of the kinds of perfumes and quantities thereof corresponding to the items therein in a computer; displaying the classification table on a retrieval menu screen; selecting a desired smell item from the classification table; retrieving perfume information corresponding to the selected smell item; selecting a specific perfume containing member from a plurality of perfume containing members by means of the smell generation control member and smell generating means based on the retrieved perfume information; and generating the smell in an amount specified by the perfume information.

According to the fifteenth aspect of the present invention, there is provided a smell generation method for generating a desired smell under a control by computer, characterized by including steps of: preliminarily registering the classification tables of smells and deodorants and perfume information and deodorant information composed of the kinds and quantities of perfumes and deodorants corresponding to the items therein in a computer; displaying the classification tables on a retrieval menu screen; selecting items of a desired smell and a desired deodorant from the classification tables; retrieving perfume information and deodorant information corresponding to the selected smell item; and by the smell generation control means, the perfume generation means, the deodorant generation control means and deodorant generating means based on the retrieved perfume information and deodorant information, selecting and releasing a specific perfume containing member from a plurality of perfume containing members so as to generate the smell in an amount specified by the perfume information; while selecting and releasing a specific deodorant containing member from a plurality of deodorant containing members so as to generate the deodorant in an amount specified by the deodorant information.

According to the sixteenth aspect of the present invention, there is provided a smell generation method, characterized in that the perfume information is composed of the kinds of perfumes, the quantities thereof and changes of these situation over time.

According to the seventeenth aspect of the present invention, there is provided a smell generation method, characterized by, after generating a smell, correcting the perfume information so as to make this smell to be a desired one, registering it, and generating a smell based on the corrected perfume information.

According to the eighteenth aspect of the present invention, there is provided a smell generation method, in which the deodorant information is composed of the kinds of deodorants, the quantities thereof and changes of these situation over time.

According to the nineteenth aspect of the present invention, there is provided a smell generation method, characterized by, after generating a smell, correcting the deodorant information to make this smell to a desired one, registering it, and generating a smell based on the corrected deodorant information.

According to the twentieth aspect of the present invention, there is provided a smell generation method characterized by generating a smell corresponding to each frame of a continuous plurality of frames of image and/or sound.

According to the twenty first aspect of the present invention, there is provided a smell generation method, characterized by, after generating a smell corresponding to each frame of the continuous plurality of frames of image and/or sound, correcting the perfume information so as to make this smell to be a desired one synchronous with image and/or sound, registered it, and generating a smell based on the corrected perfume information.

According to the twenty second aspect of the present invention, there is provided a smell generation method, characterized by, after generating a smell corresponding to each frame of the continuous plurality of frames of image and/or sound, correcting the deodorant information so as to make this smell to be a desired one synchronous with image and/or sound, registering the smell, and generating a smell based on the corrected deodorant information.

According to the twenty third aspect of the present invention, there is provided a smell generation method, characterized by installing the smell generating apparatus at a plurality of places, and generating the smell generated according to the smell generation method using at least an apparatus at one place, also at an apparatus at least another place through communication means connecting the individual apparatuses.

According to the twenty fourth aspect of the present invention, there is provided a smell generation method, characterized by, after generating a smell, generating deodorant when a predetermined time has elapsed.

According to the twenty fifth aspect of the present invention, there is provided a smell generation method in which deodorant is generated from the deodorant generating means using at least any one of the deodorant information registration means, deodorant information extracting means, deodorant generation control means and deodorant selecting means.

According to the twenty sixth aspect of the present invention, there is provided a smell generation method, characterized by connecting the smell generating apparatus to a computer system provided with the perfume containing member (A) and the smell generating means (E) for generating a smell through communication means, and transmitting the perfume information with the software related to the perfume information from the smell generating apparatus to the computer system so as to generate a smell from the smell generating means of the computer system.

According to the twenty seventh aspect of the present invention, there is provided a smell generation method, characterized by connecting the smell generating apparatus to a computer system provided with the perfume containing member (A), the deodorant containing member (A'), the smell generating means (E) and the deodorant generating means (E') through communication means, transmitting the perfume information and deodorant information with the software related to the perfume information and deodorant information from the smell generating apparatus to the computer system so as to generate a smell from the smell generating means of the computer system and subsequently generate deodorant.

According to the twenty eighth aspect of the present invention, there is provided a smell generation method in which, when transmitting and/or receiving the perfume information and deodorant information, an address is provided to each of a combination of the kind and usage amount of a perfume to be transmitted and/or received, a combination of the kind and usage amount of deodorant, and a combination of the perfume and deodorant, and a smell corresponding to the address is generated on the reception side by transmitting/receiving the address.

According to the twenty ninth aspect of the present invention, there is provided a smell generation method, in which the perfume information is encrypted, compressed and transmitted, and the encrypted perfume information is uncompressed and decrypted with specialized uncompression/decryption software.

BEST MODE FOR CARRYING OUT THE INVENTION

Figure 1:
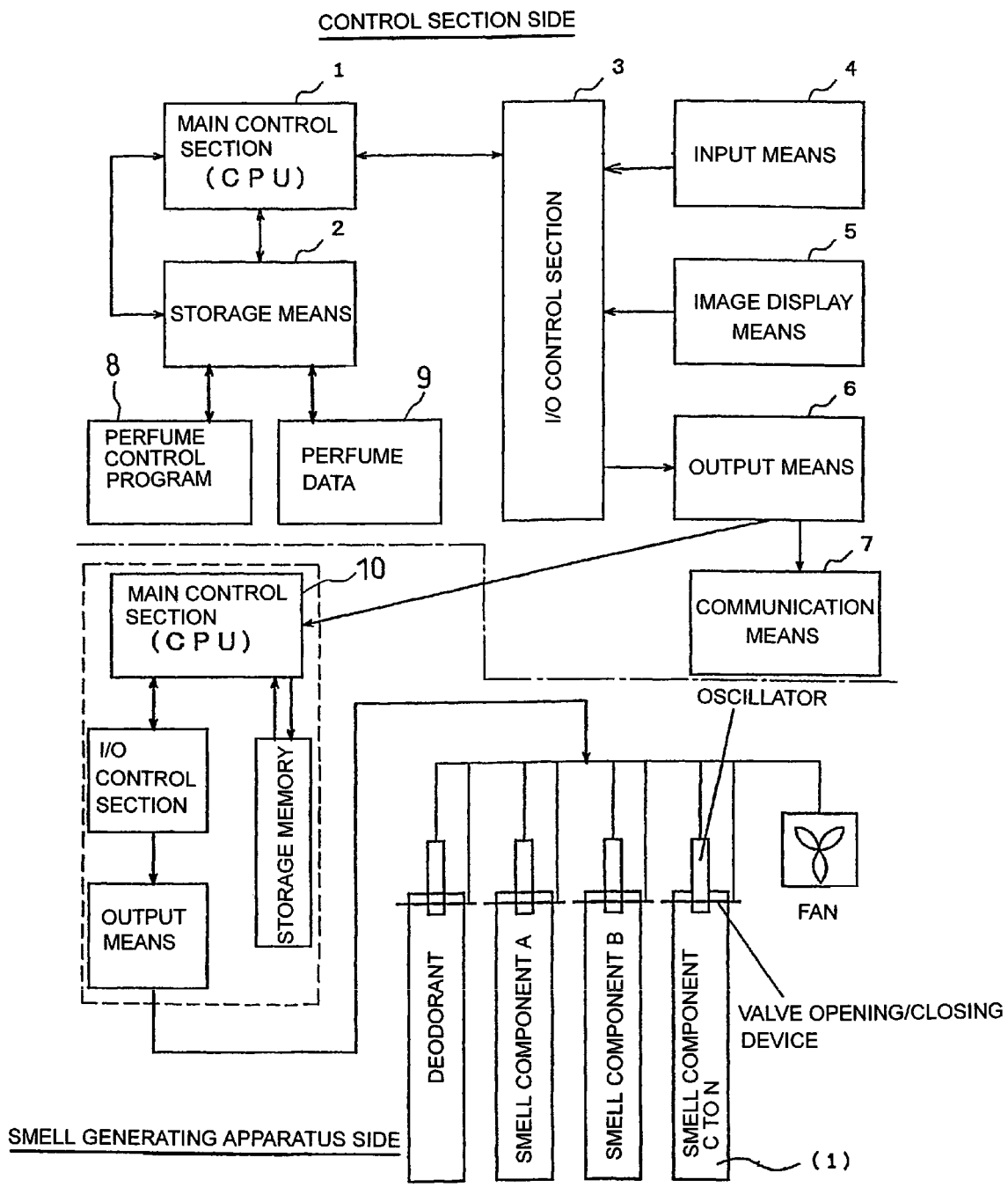
FIG. 1 is a hardware configuration diagram showing schematically a first embodiment of the present invention as a model.

FIG. 1 is a hardware configuration diagram showing schematically an embodiment of the present invention as a model. This diagram shows a schematic configuration of an apparatus for generating the smell component for generating perfume and the smell of deodorant independently or by mixing them. A main control section 1 controls the entire system and is connected to storage means 2 for storing various kinds of programs and an I/O control section 3. A storage section 8 in which perfume control program is stored is connected to the storage means 2 and additionally, a perfume data storage section 9 is connected thereto and data in these storage sections is called appropriately by a program of the main control section 1 for use.

Input means 4, image display means 5, output means 6 and communication means 7 are connected to the I/O control section 3. The input means 4 generates perfume or deodorant selectively and a keyboard, a mouse or the like is used for the purpose. The image display means 5 displays perfume or deodorant smell generating data and a screen (moving picture or other image) to be displayed with generation of perfume and is used for control of combination thereof.

The output means 6 outputs a signal for generating various kinds of perfumes or smell of deodorant and is connected to the control section 10 for generating smell. The I/O control section, output means connected thereto and a storage memory are connected to the control section 10 in order to control a smell generating device to be described later.

According to the present invention, a perfume container may be used as the perfume containing member (A). Although the perfume container is not limited to any specific type as long as it can be closed tightly, a replaceable cartridge is preferable for convenience of replenishment, exchange and the like. Each cartridge is controlled based on its numbering system and/or its own different configuration in order to prevent such an error as misidentification, mixing of respective perfumes. Although a single perfume container can store liquid perfume compound or a single perfume compound dissolved in volatile solvent, it can also store perfume composition obtained by blending a plurality of perfume compounds. For example, it may contain sea or seaside perfume or forest perfume. The perfume to be contained in the perfume container may be of any kind, for example, liquid, paste-like, solid, powder and the like or perfume component may be soaked in or adhered to solid such as fiber-like substance. Alternatively, a solid metal may be used as the perfume container. By heating this, smell of burnt metal can be generated. Like this, because the perfume is a source for generating some kind of smell, everything capable of generating a smell can be adopted without sticking to a conventional concept about the perfume. Because the quantity of the perfume containers is naturally restricted by the size of the entire apparatus, preferably, a perfume compound or a perfume composition to be stored in the perfume container is selected so as to generate the most effective smell within that restriction. Although usually, the perfume container includes ten or several tens capsules each containing a specific perfume upon actual use, it is permissible to add an arbitrary number of empty capsules to the set so as to conform to user's taste. Consequently, a user can synthesize a desired smell by adding his or her desired perfumes. In this case, it is necessary to add software about handling of the added perfume.

The deodorant containing member (A') may be a deodorant container, the basic conditions are substantially the same as for the case of the perfume container.

Although there is not a restriction, the smell generating means (F) and the deodorant generating means (U) may be an apparatus which can apply ultrasonic vibration, heating, pressure, wind or other means independently or in combination to the perfume containing member or the deodorant containing member, and consequently, perfume or deodorant contained in the perfume containing member or deodorant containing member can be discharged outside. For example, the ultrasonic wave oscillator, which is an example of specific means, exerts the function of stimulating perfume or deodorant with ultrasonic wave corresponding to time passage, and atomizing and emitting it by changing the voltage or frequency. As another example, it is permissible to provide a heating device around the perfume containing member or deodorant containing member. In this case, a heating device capable of transmitting generated heat immediately by using, for example, ceramics material having an excellent heat response is preferable. As an example of using pressure, a smell can be generated toward outside through an opening/closing port by moving a pressure valve vertically with a high frequency vibrating motor or the like. The perfume containing member and the deodorant containing member are obviously provided with such an opening/closing function for discharging perfume or deodorant toward outside when necessary and preventing mixing after that. If an electric opening/closing valve is used, it can be opened/closed by applying an electric signal. A type using pressure release function can utilize a rubber made valve.

The perfume containing member and the deodorant containing member can be provided with perfume generating means and deodorant generating means, respectively. Depending on the case, the perfume containing member can be integrated with the perfume generating means and the deodorant containing member can be integrated with the deodorant generating means.

In the case where the containing member and the generating means are integrated or semi-integrated, if the containing member is a container, it is inconvenient. In such a case, the perfume containing member and the deodorant containing member can be made of porous material such as metal, ceramics, plastics, plant base material, or the like. This porous material may also be used well for the case of a non-integrated type.

The porous material is coated with and/or impregnated with perfume or deodorant and the perfume or deodorant may be discharged outside by applying a rotation, vibration, heat, pressure such as wind pressure, or the like to this porous material by giving a kind of signal.

As a typical case in which the containing member and the generating means are integrated, if a wind blowing rotating body of a blade is produced using the aforementioned porous material, perfume or deodorant applied or impregnated on the rotating body can be discharged when that rotating body is rotated.

Figure 10:
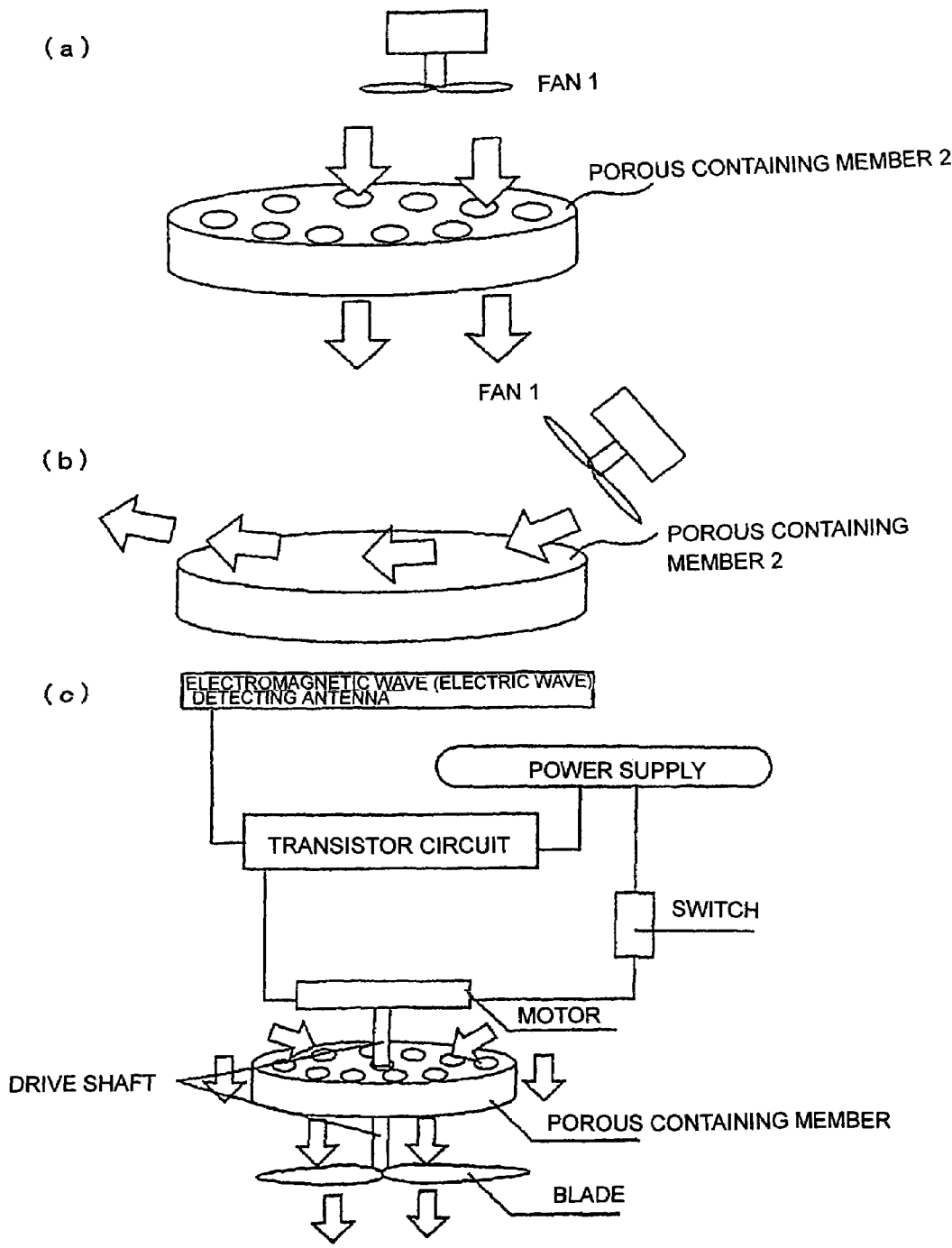
FIGS. 10(a), (b), and (c) are perspective views showing a specific example provided with a containing member coated or impregnated with perfume or deodorant in front of or at the back of an air blowing rotating body.

Although the containing member and the generating means are completely integrated if the wind blowing rotating body is made of the porous body, the semi-integrated type may be produced by disposing the porous material in front of and/or at the back of the wind blowing rotating body. FIGS. 10(a) to (c) show its specific examples.

FIGS. 10(a) and (b) show a type in which wind is applied to a containing member coated with and/or impregnated with perfume or deodorant with a fan. FIG. 10(c) shows a type in which a containing member coated with and/or impregnated with perfume or deodorant is disposed between the motor of the fan and the rotating body. More specifically, if electromagnetic wave is received from an electromagnetic wave detecting antenna, a transistor circuit is actuated so as to supply electricity of a battery portion to the motor. Then, a blade section is rotated so that perfume and/or deodorant is generated from a porous containing member. That porous containing member may be formed in a shape for holding air passage.

Figure 11:
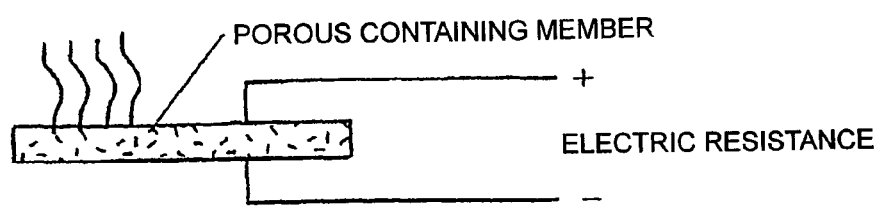
FIG. 11(a) shows a method for generating perfume or deodorant by heating a porous containing member.
FIG. 11(b) shows a method for generating perfume or deodorant by vibrating the porous containing member.
FIG. 11(c) shows a method for generating perfume or deodorant by rubbing the porous containing member.
Figure 11:
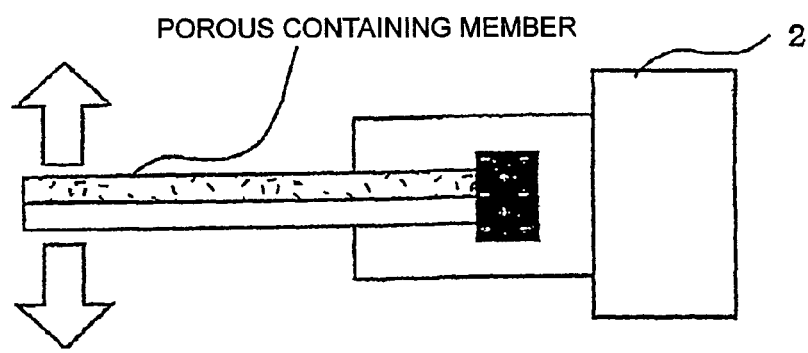
Figure 11:
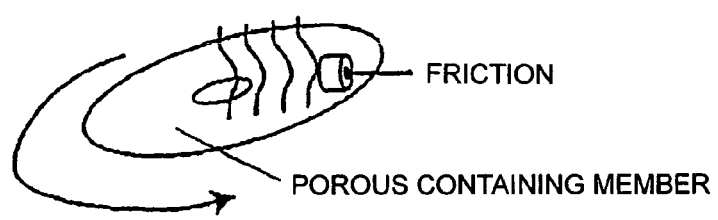

Perfume or deodorant can be generated from a containing member when the containing member coated with and/or impregnated with perfume or deodorant or a laminated body containing this containing member is vibrated, heated or rubbed by supplying electric power corresponding to a generation signal to the containing member or the laminated body. FIGS. 11(a) to (c) show its specific example. FIG. 11(a) shows a type in which a conductive porous body is impregnated with perfume or deodorant and perfume or deodorant is vaporized by heating the conductive porous body by supplying current thereto. FIG. 11(b) shows a type in which the nonconductive porous body and conductive laminated body are used and the conductive body is heated like FIG. 11(a). FIG. 11(c) shows a type in which perfume or deodorant in the porous body is vaporized by friction between the porous material and the friction member.

In the case of FIG. 4(a), perfume A is generated and perfume B is generated during generation of the perfume A. Then, generation of the perfume A is stopped while perfume B is generated. Perfume C is generated during generation of the perfume B. Then, generation of the perfume B is stopped and after a while, generation of the perfume C is stopped. The basic pattern is constituted by repeating the above-described cycle after a short stop. In this case, deodorant may be generated in this short stop period. Consequently, the perfume up to then can be vanished completely before a next cycle is started.

FIG. 4(b) shows a method for continuing generating deodorant of a constant amount with the pattern of FIG. 4(a). According to this method, for example, in FIG. 10(a) or (b), a fan is made of a porous member, or a porous member is bonded to the fan and is impregnated with deodorant. On the other hand, the porous containing member 2 is impregnated with perfume and if the fan is rotated, perfume component and deodorant component are discharged outside simultaneously. Consequently, after perfume is recognized by the sense of smell, that perfume is vanished so that the response of a perfume generating system is raised with time. Further, the deodorant exerts the function for weakening other perfumes floating outside, so that this deodorant can support man's sensing of the discharged perfume as intended.

Figure 12:
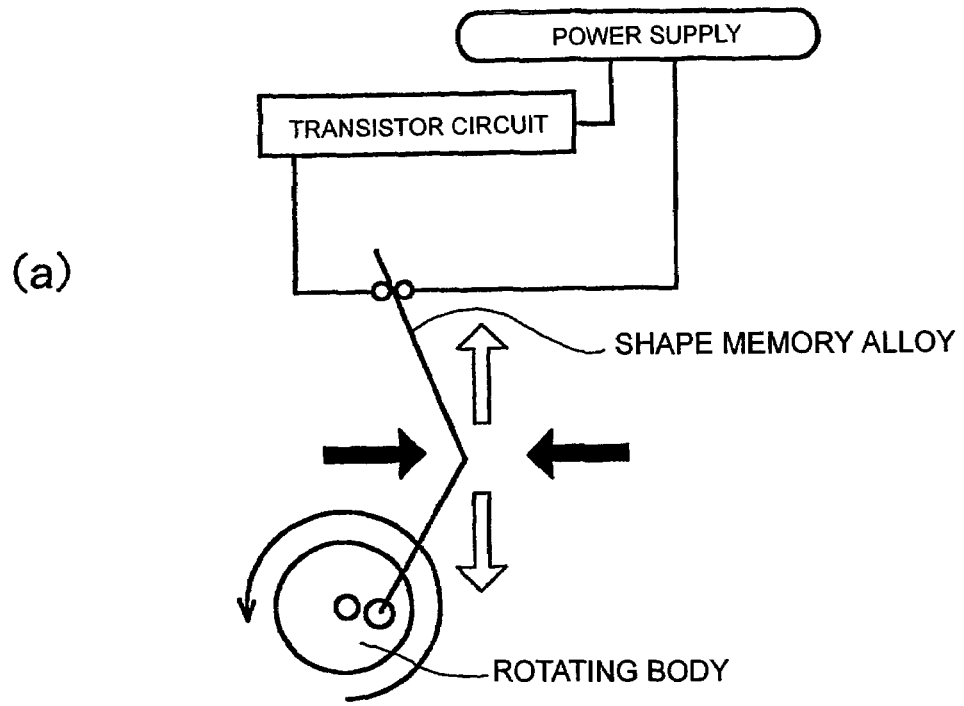
FIGS. 12(a) and (b) show methods for generating perfume or deodorant by vibrating or rubbing the porous containing member using shape memory alloy.
Figure 12:
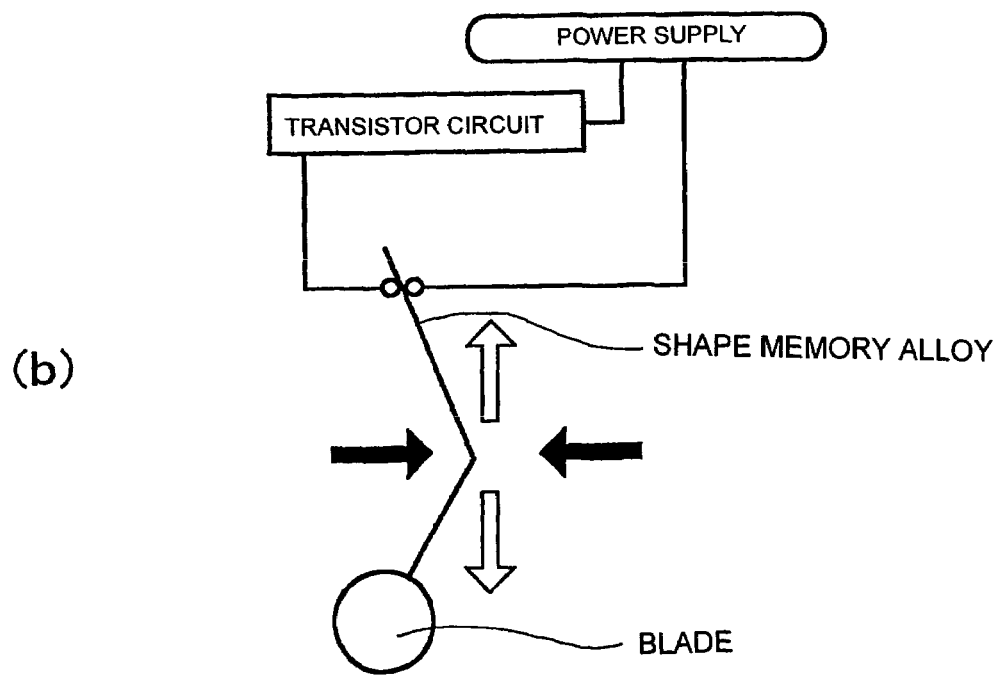

FIGS. 12(a) and (b) show a method in which a shape memory alloy is used in place of a fan. This method utilizes the shape memory alloy whose shape is changed when heat is applied or current is supplied and returned to its original shape if heat or current is interrupted. By applying heat or current intermittently so as to bend the shape memory alloy in the shape of letter V or in a shape of a straight line (vertical and horizontal arrows in FIGS. 12(a) and (b) indicate the motion of the shape memory alloy) and according to FIG. 12(a), perfume or deodorant is generated by rotating a porous rotating body impregnated with perfume or deodorant, while according to FIG. 12(b), perfume or deodorant contained in the porous blade is vaporized by vibrating the porous blade attached to a disc.

The perfume generating control means (D) selects a necessary perfume corresponding to an instruction on a specific perfume based on perfume classification table, the amount of its generation, and a condition for changing that generation amount over time. As necessary, it generates a perfume according to this selection condition and simulates (operates) correcting the respective selection condition based on its result. Although this simulation may be carried out on the condition for generating only the perfume, the simulation may be carried out by combination of image and/or sound (including music). If information selective extracting means (C) based on perfume information registration means (B) which stores a setting condition through input means such as a keyboard, mouse and editing work (extraction and calculation of storage data) which is an execution action are carried out, an instruction (command) on perfume generation control is executed.

The deodorant generation control means (S) selects a necessary deodorant corresponding to an instruction on a specific deodorant based on deodorant classification table, the amount of its generation, and a condition for changing that generation amount with time. It generates perfume and deodorant by combination of the perfume generation selection condition and deodorant generation selection condition and simulates to correct the respective selection conditions based on its result. Although this simulation may be carried out only by combination of the perfume generation and deodorant generation, the simulation may be carried out by combination of image and/or sound (including music). If the deodorant information selective extracting means (R) based on deodorant information means (Q) which stores the setting condition through input means such as keyboard, mouse and the editing work are executed, an instruction (command) on deodorant generation control is carried out.

The perfume generation control means set up in this way is stored in appropriate storage means. If the instruction (command) on smell generation control is executed with a smell generation program after the editing work (extracting, calculation and the like of storage data) based on the perfume information registration means (B) is carried out, the perfume generation control mean controls the smell generating means through means for converting the amplified amount of the frequency or digital signal to the magnitude of voltage using a transistor integrated circuit incorporated in the main control section of a computer or switching means for generating and transmitting voltage A, voltage B, . . . to voltage N with a circuit for supplying a plurality of currents based on electric signal from the transistor integrated circuit. The means like above can increase/decrease the number of vibrations of an ultrasonic wave generating device in the smell generating means, the amount of heat in a heating device or the degree of pressure of a pressure applying device. The means like above may be used independently or by combination. If the means like above is used by combination with another means, it is necessary to provide a branch circuit for actuating those devices at the same time according to a determined standard. Unless the aforementioned respective signals are sent, the smell generating means is stopped.

The preset deodorant generation control means is stored in memory means. If the instruction (command) on deodorant generation control is executed with a deodorant generation program after the editing work (extracting, calculation and the like of storage data) based on the deodorant information registration means (Q) is carried out, the deodorant generation control mean controls the deodorant generating means through means for converting the amplified amount of the frequency or digital signal to the magnitude of voltage using a transistor integrated circuit incorporated in the main control section of a computer or switching means for generating and transmitting voltage A, voltage B, . . . to voltage N with a circuit for supplying a plurality of currents based on electric signal from the transistor integrated circuit. The means like above can increase/decrease the number of vibrations of an ultrasonic wave generating device in the deodorant generating means, the amount of heat in a heating device or the degree of pressure of a pressure applying device. The means like above may be used independently or by combination. If the means like above is used by combination with another means, it is necessary to provide a branch circuit for actuating those devices at the same time according to a determined standard. Unless the aforementioned respective signals are sent, the deodorant generating means is stopped.

A wind blowing device may be provided so as to feed a smell discharged by transmitting an execution command to the smell generating means (F), the smell selection means (E) and the smell generation control means (D) in a specific direction. This wind blowing device feeds the smell in the specific direction and if an instruction (command) on smell generation amount control is executed as a result of executing the editing work (extraction, calculation and the like of storage data) based on the storage means, can increase/decrease or stop the motor revolution number of the wind blowing device by cooperation with the function for generating and transmitting voltage A, voltage B, . . . to voltage N by switching by connecting it to a circuit for converting the amplification amount of the frequency or digital signal to the magnitude of the voltage or supplying a plurality of currents based on electric signal from a transistor integrated circuit. Consequently, the use of the wind blowing amount can be changed without any step and thus, the far-and-near feeling of a smell can be generated such that the smell approaches from afar or the smell faded away in the distance. The number of the smell discharging port may be one or more, and each position may be fixed or movable.

A wind blowing device may be provided so as to feed a deodorant discharged by transmitting an execution command to the deodorant generating means (U), the deodorant selection means (T) and the deodorant generation control means (S) in a specific direction. This wind blowing device feeds the deodorant in the specific direction and if an instruction (command) on deodorant generation amount control is executed as a result of executing the editing work (extraction, calculation and the like of storage data) based on the storage means, can increase/decrease or stop the motor revolution number of the wind blowing device by cooperation with the function for generating and transmitting voltage A, voltage B, . . . to voltage N by switching by connecting it to a circuit for converting the amplification amount of the frequency or digital signal to the magnitude of the voltage or supplying a plurality of currents based on electric signal from a transistor integrated circuit. The number of the deodorant discharging port may be one or more, and each position may be fixed or movable.

To control the kinds of infinite number of smells, a smell classification table is determined preliminarily by using the perfume information selective selection means (C). Then, it is necessary to store what smell is produced by discharging which perfume from the respective perfume containing members A, B, C to N by how much in storage means, for example, a hard disc or server. This corresponds to the perfume information registration means (B). Although the classification table may be a single one which allows specifying 10 to 50 kinds of perfumes directly (1), it is permissible to create a high level classification table and lower level classification tables in which the higher level concept is expanded to lower level concepts so that a smell matching his or her own feeling in terms of image or music better can be obtained (2).

To control the kinds of infinite number of smells, in addition to the aforementioned means, a deodorant classification table is determined preliminarily by using the deodorant information selective selection means (R). Then, it is necessary to store what smell is produced by discharging which perfume from the respective deodorant containing members A, B, C to N by how much in storage means, for example, a hard disc or server. This corresponds to the deodorant information registration means (Q). Although the classification table may be a single one which allows specifying a specific deodorant (1), it is permissible to create a high level classification table and lower level classification tables in which the higher level concept is expanded to lower level concepts so that a deodorant effect matching his or her own feeling in terms of image or music better can be obtained (2).

As a plurality of classification tables using the high level concept and the lower level concept, an extremely higher conceptual basic classification (for example, as classification items, human matter, natural matter, environmental matter, cultural matter and the like can be exemplified), expanded classification corresponding to lower concepts of these classification items (for example, as the lower concepts of human matter item, such classification items as male and female matter, friend matter, family matter can be mentioned), and expanded classifications corresponding to lower concepts of these items (for example, as the lower concept of the male and female matter, lover, pure love, lost love, husband and wife and the like can be mentioned) can be picked up. Depending on the case, as much lower expanded classifications, specific perfumes can be set up as items A, B, C . . . for a person who cannot imagine a perfume corresponding to the "pure love".

Further, a classification table capable of pointing out only specific perfumes can be used for the beginners. As the classification table of these smells, following major classification and minor classifications indicated in the parentheses can be mentioned: for example, (A) natural perfume as a major classification item (more specifically, perfumes giving atmosphere corresponding to such items as rose, plain, forest, sea, seaside, wind, animal, mineral and the like), (B) urban perfume as a major classification item (more specifically, perfumes giving atmosphere corresponding to such items as street trees, buildings, office, asphalt, road, exhaust gas, crowd, automobile, train), (C) abstract perfume as a major classification item (more specifically, perfume giving atmosphere corresponding to affection, joy, health, love, purity, enthusiasm, stress, freshness, anxiety, unhappiness). Perfume information registration means (B) for registering the smell classification table mentioned in claim 4, the kinds of perfumes set preliminarily corresponding to the smell items in the smell classification table, the generation amount, preset information on the changing amount of that generation amount over time, and perfume information (simulation) modified after that is required. Consequently, a desired smell can be generated by storing these data in storage means and using a design software corresponding to that perfume information selecting and extracting means (C) obtained in the above way.

Although the perfume generation source is mainly perfumes, this is not restricted to these. It is permissible to use methyl mercaptan said to be near the smell of a rest room, curry powder, or exhaust gas of automobile as a perfume source.

The amount of a smell discharged from a perfume containing member is expressed in a numerical value of 10 stages and this numerical data is programmed in a memory which is the storage means (D) for controlling the perfume discharge and stored temporarily. This is the smell generation program storage means (G). If the data is specified to for example 5 of the 10 stages using this storage means, this given value is stored temporarily in a memory holding device (for example, hard disc) in a computer or a memory holding device (for example, hard disc, server, MO, CD and the like) connected to the external. Further, it is stored in a memory within the computer temporarily. Next, the computer activates the smell selection means (E), the smell generating means (D) and the smell generation control means (D) so as to transmit the value 5. For this transmission, external transmission software like driver software for actuating an external printer by means of a computer is used.

The amount of a deodorant discharged from a deodorant containing member is expressed in a numerical value of 10 stages and this numerical data is programmed in a memory which is the deodorant storage means (S) for controlling the deodorant discharge and stored temporarily. This is the generation program storage means (V). If the data is specified to for example 5 of the 10 stages using this storage means, this given value is stored temporarily in a memory holding device (for example, hard disc) in a computer or a memory holding device (for example, hard disc, server, MO, CD and the like) connected to the external. Further, it is stored in a memory within the computer temporarily. Next, the computer activates the deodorant selection means (T), the deodorant generating means (S) and the deodorant generation control means (S) so as to transmit the value 5 as aforementioned. For this transmission, external transmission software like driver software for actuating an external printer by means of a computer is used.

Figure 2:
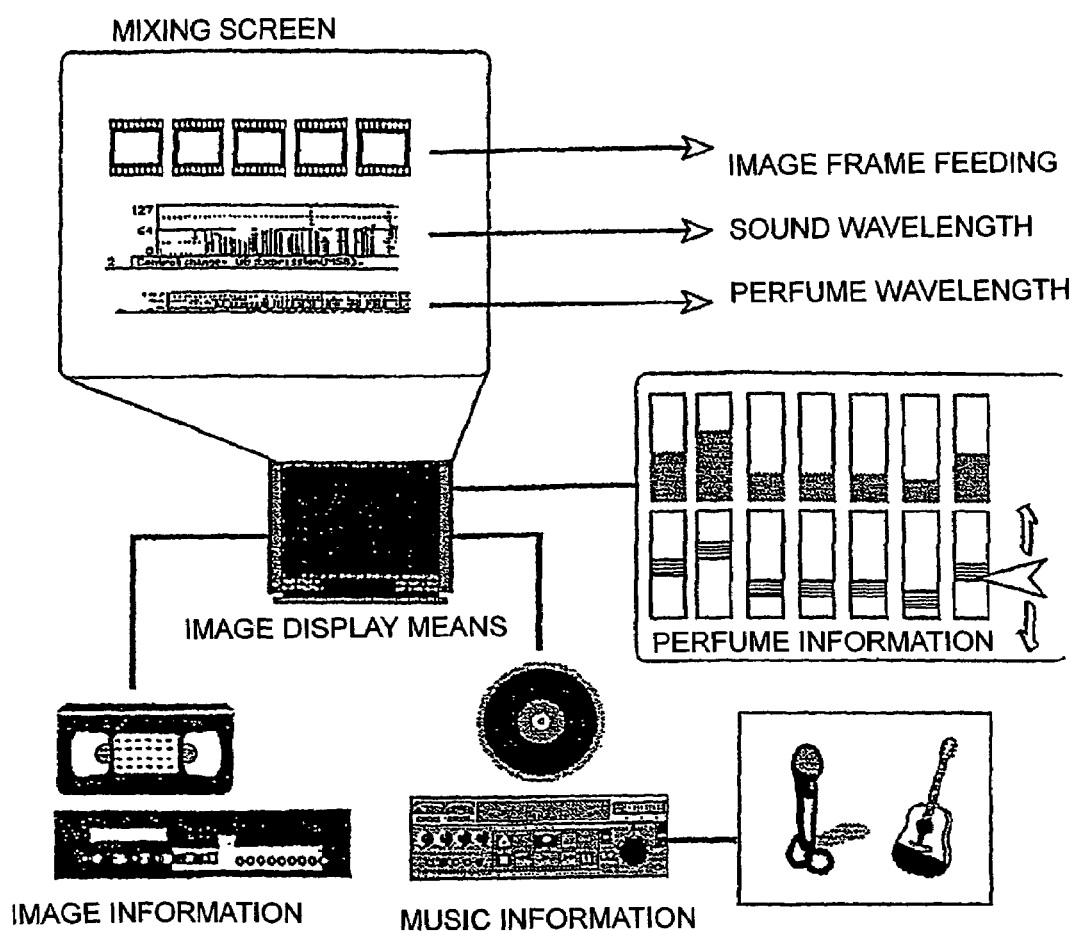
FIG. 2 is a conceptual diagram for mixing smell data, image data and sound data.

To produce a smell similar to a desired one by executing the smell simulation with the computer software, a retrieval screen can be prepared as the major classification. For example by selecting and retrieving the concept of flower perfume, sea perfume, forest perfume or the like, perfume data (for example, the flower perfume is obtained by mixing level 10 of perfume A and level 3 of perfume C) stored preliminarily as data by the perfume information registration means (B) can be corrected while sensing a smell generated from the smell generating apparatus by changing with a mouse or a keyboard the waveform or bar code (indicated on the screen) of perfume A, perfume B, perfume C, perfume D to perfume N disposed in parallel as shown in FIG. 2 (see FIG. 5 also which is the flow chart of FIG. 2) like music mixing operation (multiplication of waveforms described on pages 98 to 99 of DTM Magazine Vol. 69, No. 3, published by Terashima Joho Kikaku Co., Ltd. titled "Lecture on Musical Tone which can be studied by seeing and listening, No. 17"). This is achieved by the perfume information selecting and extracting means (C). As other example, a simple simulation capable of introducing a result easily can be prepared by preparing a number of samples. This operation corrects a smell changing over time as digital signal and its data can be stored in an arbitrary memory holding device.

To produce a smell/deodorant condition similar to a desired one by executing the deodorant simulation with the computer software, a retrieval screen can be prepared as the major classification. For example by selecting and retrieving the concept of flower perfume, sea perfume, forest perfume or the like, perfume data (for example, the flower perfume is obtained by mixing level 10 of perfume A and level 3 of perfume C) stored preliminarily as data can be corrected while sensing a smell generated from the smell generating apparatus by changing the waveform, bar code (indicated on the screen), the kind and quantity of the deodorant of perfume A, perfume B, perfume C, perfume D to perfume N disposed in parallel with a mouse or a keyboard as shown in FIG. 2 (see FIG. 5 also which is the flow chart of FIG. 2) like music mixing operation (multiplication of waveforms described on pages 98 to 99 of DTM Magazine Vol. 69, No. 3, published by Terashima Joho Kikaku Co., Ltd. titled "Lecture on Musical Tone which can be studied by seeing and listening, No. 17"). This is achieved by the perfume information selecting and extracting means (C) and the deodorant information selective extracting means (R). As other example, a simple simulation capable of introducing a result easily can be prepared by preparing a number of samples. This operation corrects a smell changing over time as digital signal and its data can be stored in an arbitrary memory holding device.

Figure 4:
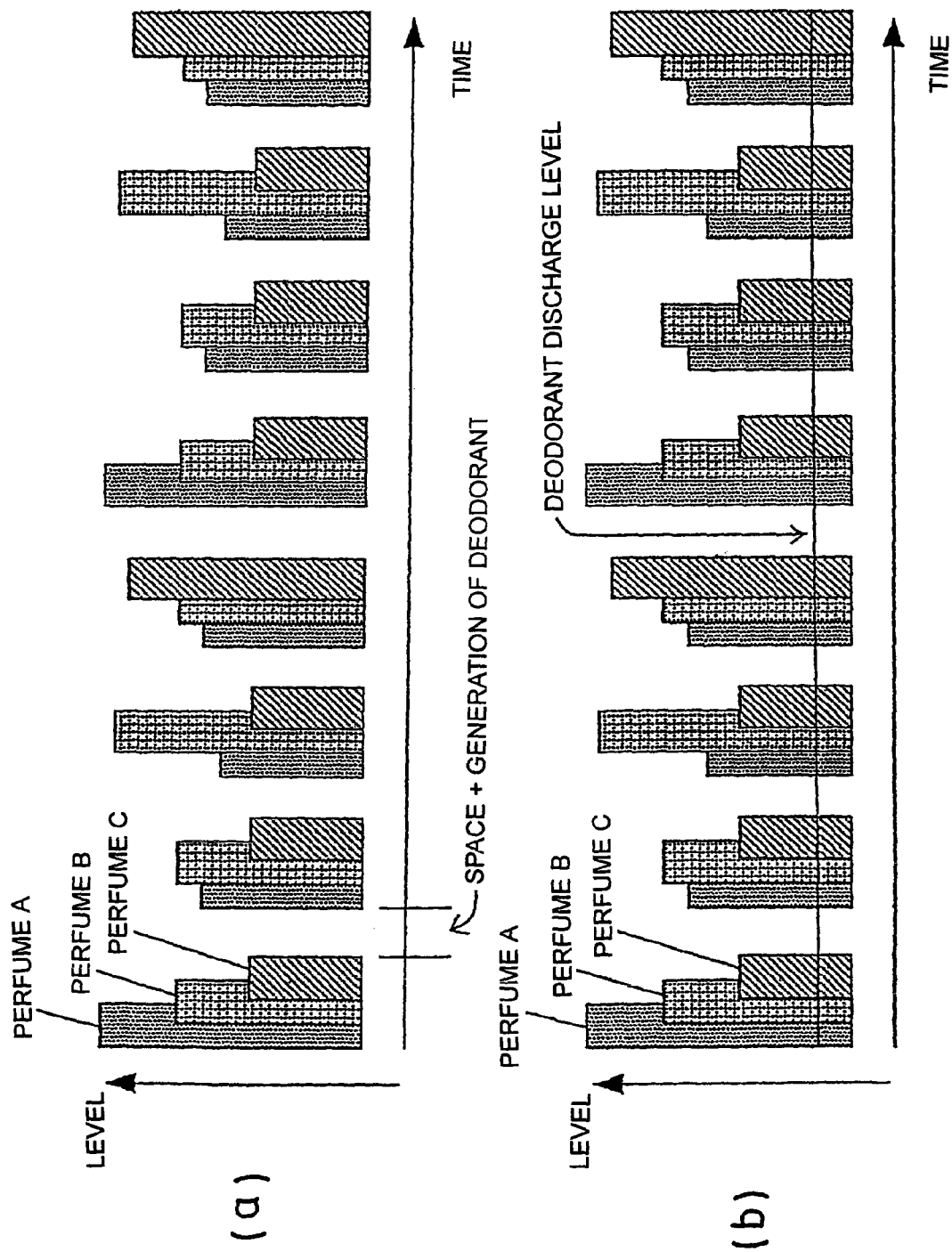
FIG. 4 is an enlarged diagram of the "perfume wavelength" of FIG. 3.

The synthesizing work (mixing) of smells input through a keyboard or a mouse is similar to the musical mixing work. That is, in the case of music, the sound of each part or each of such instruments as base guitar, lead guitar, piano, drum, vocal is played in parallel to each other on the horizontal axis and the respective parts are mixed (chord) on the vertical axis so as to play a music. In the world of smells, each perfume container plays the same role as a musical instrument. For example, in FIG. 4, each block on the horizontal axis contains a plurality of perfumes discharged from respective perfume containers (FIG. 4 shows three kinds of perfumes emitted from three perfume containing members). The horizontal axis indicates a time passage while the vertical axis indicates its emission amount or the intensity of a smell. This smell mixing work forms the bar code or waveform vibration like producing a music by mixing respective parts adopted in the today's musical world. These are controlled as digital signals. That is, the smell mixing work is operated based on each of the perfume containing members. Upon mixing, a mixing board is displayed on the control screen. To support the mixing, the mixing control unit can be supported externally as well as through the input system screen. For the mixing operation, the intensity of the level can be changed by moving the level change button divided to each part vertically with a mouse or pressing a value input button (for example, button capable of expressing high or low) on the screen using a mouse or a keyboard or inputting a numerical value. The perfume contained in a perfume containing member cannot express itself but by its discharge amount and this is just like twanging a string of a guitar strongly or weakly. This intensity operates several tens kinds of the perfume containing members in various ways, so that the change of a smell generated from the smell generating device outside the computer over time can be modified in various ways depending on a creator's desire and stored in the perfume information selective extracting means (C).

There are following methods using deodorant for the synthesizing work (mixing) of smells. For example, each block on the horizontal axis contains a plurality of perfumes discharged form respective perfume containing members (in FIG. 4, three kinds of perfumes discharged from the three perfume containing members) while the horizontal axis indicates a time passage and the vertical axis indicates the emission amount or the intensity of a smell. This smell mixing work forms the bar code or waveform vibration like producing music by mixing respective parts adopted in the today's musical world. These are controlled as digital signals. That is, the smell mixing work is operated based on each of the perfume containing members and each of the deodorant containing member. Upon mixing, a mixing board is displayed on the control screen. To support the mixing, the mixing control unit can be supported externally as well as through the input system screen. For the mixing operation, the intensity of the level can be changed by changing the level change button divided to each part vertically with a mouse or pressing a value input button (for example, button capable of expressing high or low) on the screen using a mouse or a keyboard or inputting a numerical value. The perfume contained in a perfume container cannot express itself but by its discharge amount and this is just like twanging a string of a guitar strongly or weakly. This intensity operates several tens kinds of the perfume containing members in various ways, so that the change of a smell generated from the smell generating device outside the computer over time can be modified in various ways depending on a creator's desire and stored in the perfume information selective extracting means (C) and the deodorant information selective extracting means (R).

Because the image as a medium makes a viewer feel as if an object in the screen moves over time by sequentially displaying changes of a single fixed image and music is felt by listening to a change of sound source over time, it is preferable to control the kind and intensity of generated smell and deodorant over time so as to express a perfume integrally with a generated smell and deodorant.

According to the present invention, as regards the generation of a smell generated continuously or discontinuously, if a smell is left so that a newly generated smell is mixed with the residual smell, an object smell may not be obtained. In such a case, preferably, deodorant is released from the deodorant containing members so as to remove the left smell and then a new smell is released. Further, to produce a smell as close to an object smell as possible, an appropriate space is provided between waveforms or bars as shown in FIG. 4(A), that is, a "space" is formed so as to avoid mixing of the initial value of the smell with its final value. Further, it is permissible to always generate deodorant continuously as shown in FIG. 4(B). When deodorant is always emitted as above, (1) if an inhibition factor or an inhibiting smell existing in the space can be removed preliminarily, a generated smell can be felt more clearly;

(2) in the case where smell component and deodorant coexist, if the smell is deodorized and dissolved after it is recognized with the sense of smell, its mixing smell is expelled, so that a change of the smell can be expressed more clearly; and (3) if deodorizing is always carried out the spray amount of the deodorant is increased, and if deodorant is emitted intermittently the capacity for eliminating and dissolving a smell in a room is increased.

Upon carrying out the present invention, the first problem is what a fundamental smell and deodorant should be, in other words, what perfume should be loaded in each perfume containing member and what deodorant should be loaded in each deodorant containing member. One simple method is to charge each of the perfume containing members with several kinds of typical components recognized in the field of perfume, for example, basic perfumes such as floral type, oriental type, chypres types, fougere types. Because there is a completely different world from the perfume in the world of the smell, it is preferable to prepare such smells separately. Such smells include smells of coffee, curry, Chinese noodle, automobile exhaust gas smell, rest room smell and the like. Therefore, it is preferable to load these smells in the perfume containing member.

Because there are diversified needs in the world of the smell, it is preferable to prepare not one smell classification table or deodorant classification table, but multiple tables. Depending thereon, the perfumes loaded in the perfume containing member and the deodorants loaded in the deodorant containing member differ. Therefore, it is preferable to consider the combination of the perfume containing members and the combination of the deodorant containing member which befits each need. For the reason, it is preferable to prepare various types of classification tables, as many kinds of the perfume containing members and deodorant containing members as possible, and various kinds of software independently or by set. In this case, the perfume containing member, deodorant containing member and corresponding software can be controlled according to a specific name and number.

When transmitting or receiving signals through the Internet or portable phone, it is mandatory to use a telephone company's cable and facility stipulated legally. In this case, an independent smell dedicated transmitting/receiving language (protocol) can be determined with transmission protocol. When transmitting through a telephone company, it is preferable to attach a specific name and number to the perfume containing member, the deodorant containing member and their software. In this case, when, for example, the level (for example, data on the concentration or change over time) thereof is divided to 10 steps and 10 types of perfumes whose combination with a smell is recognized preliminarily are assumed even if numerals are determined freely in correcting operation for the perfume, a communication address is automatically obtained by conversion so that the same smell as a transmitter can be sensed by a receiver by providing a condition for each kind of perfume to be generated according to a level independently or a program for converting to an address set up preliminarily according to a numeral obtained by factorial of the combination.

The image displaying means displays the content of this system. This is executed by a liquid crystal display connected to a computer or a display unit represented by a cathode-ray tube. This displays system startup by indicating a start button, selection of operation content, extraction of memory information, retrieval, output of a result, storage, distribution of information through multi-media and the like. Current computer is capable of executing a further complicated procedure easily by using the pointer of a mouse. Further, the image display means can be replaced by a TV screen at a distribution destination of produced media, which is capable of displaying transmitted information.

Figure 5:
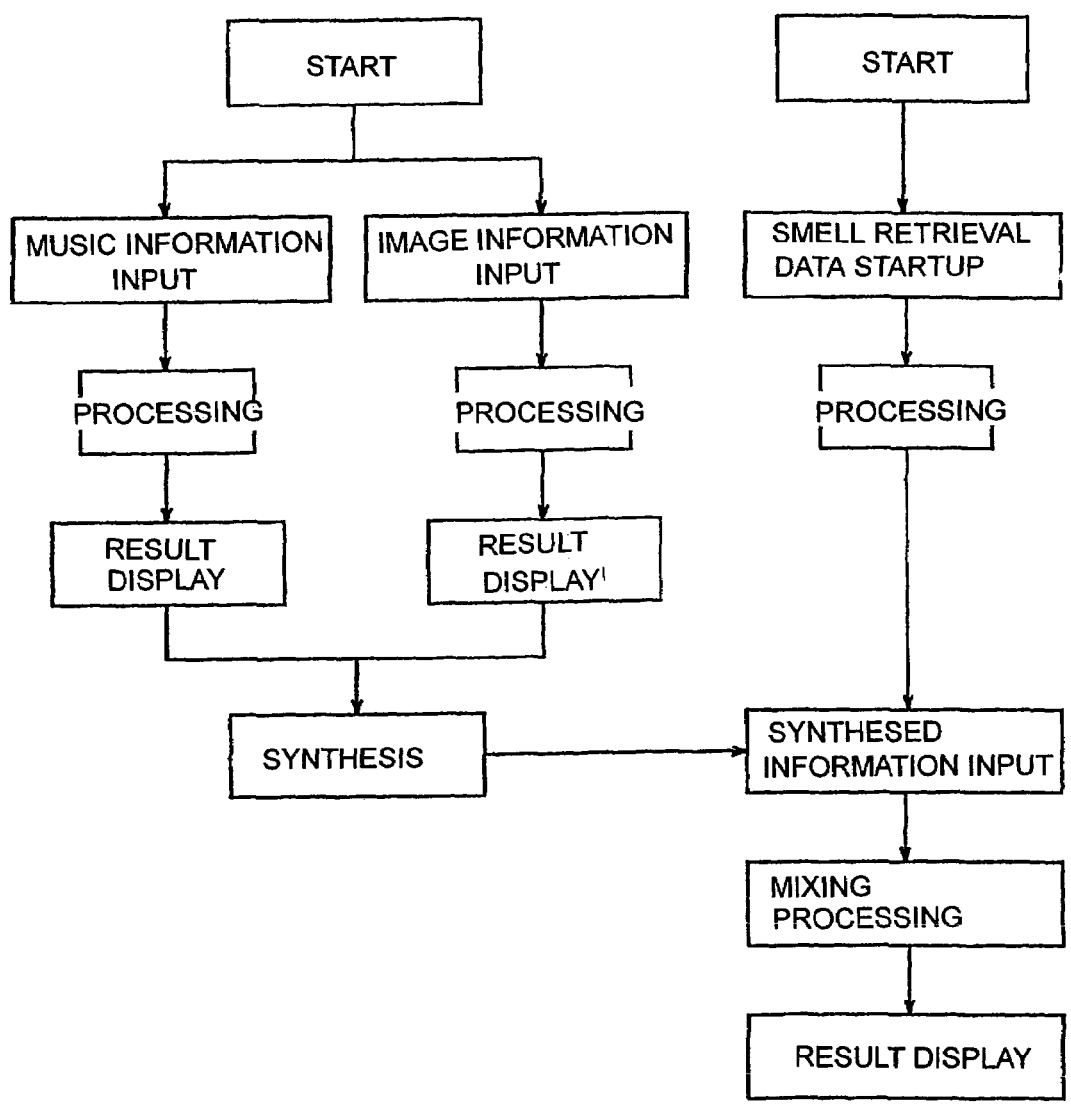
FIG. 5 is a flow chart of FIG. 2.
Figure 6:
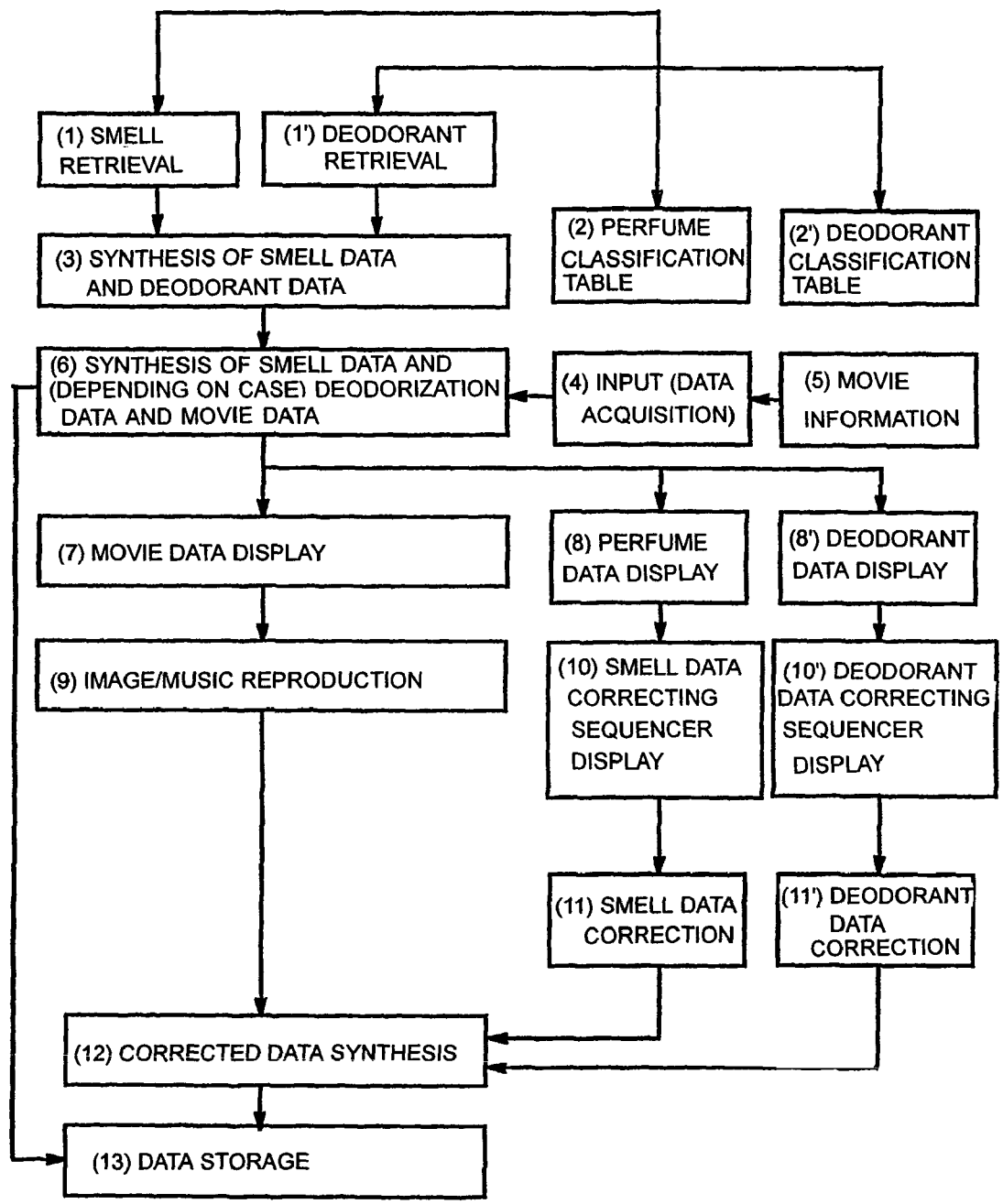
FIG. 6 is a flow chart showing mixing steps.

More specifically, an example of the procedure for producing a smell corresponding to an image or music will be described with reference to FIGS. 2, 3 and 5. Image/music data is built up through a video camera and stored in a memory of computer through a cable or stored in a hard disc. First, image information and sound information is grabbed into the hard disc of computer and its image processing screen is activated (started). Characters and other images or computer graphics image are inserted. Next, a music processing screen is started. Because the sound of the video camera has a poor quality, the sound quality is made clear by mixing with other music player. Further, an effect sound is inserted as required and can be integrated (synthesized) through the movie software. After this sequential movie creation procedure with images and music is completed, this is stored into a hard disc and after that, creation of a smell is started. Basically, the present invention can be carried out according to the mixing procedure shown in FIG. 6.

Everyone can extract data of the perfume classification table (2) determined by a specialist according to the perfume retrieval (1). For selection of deodorant, data of the deodorant classification table (2') can be extracted according to the deodorant retrieval (1') as required. The extracted perfume data is corrected in (3). Further, deodorant data can be corrected in (3') as required. The standard determined by the third party is corrected by a person who intends to create a perfume according to his feeling. Subsequently, movie data in which images and sound are integrated is grabbed into his own computer or perfume software and a deodorant software as required (4). Data created in (3) and deodorant data are synthesized with the movie data. This synthesis mentioned here means to display the movie data, perfume data and as required, deodorant data on the same table (screen). Next, the movie data is displayed (7) so that images and music are reproduced (9). In this reproduction work, the procedures for reproduction and stop are repeated. Subsequently, the perfume data and as required, deodorant data are displayed (8), (8'), and at the same time, perfume control screen, namely, perfume data correction sequencer and as required, deodorant data correction sequencer are displayed (10), (10'). Through this perfume control screen, correction of perfume data and as required, correction of deodorant data are carried out (11), (11') and synthesis corresponding to changes of perfume over time is carried out corresponding to the screen for reproduction and stop of images and music. The perfume control (10) (sequencer) plays a major role of this work and synchronizes perfume data with the movie data and as required, deodorant data by moving an image, music, perfume and as required, deodorant relatively.

The system design software of the perfume or the system design software of the deodorant is software for creating a sequence of programmed perfumes or generating a sequence of programmed deodorants without any combination of the perfume or with the combination thereof. The software as above does not only carry out basic works such as retrieval, synthesis, re-assorting but also supports an operation for clarifying the target of an object perfume further. This software can be installed from such an outside media as CD and upon recording, can be divided to smell generation control program for system retrieval, perfume classification program and deodorant generation control program, deodorant classification program data.

If explaining more in detail, first, the smell system design software and as required, deodorant system design software are activated (started). The perfume retrieval screen and as required, the deodorant retrieval screen are started. A perfume is roughly oriented by using the perfume classification table (for example, FIG. 7) and as required, the deodorant classification table so as to point out an approximate item. For example, if a scene of talking lovers with classic music is created in a movie, first, human matter item is specified as a major classification, second male and female matter item is specified as an intermediate classification and next, lover item is specified as a minor classification. At this time, a smell generating device including a plurality of perfume containing members (A), smell generating means (E), smell selection means (F), smell generation amount control means (D), a plurality of deodorant containing members (A'), deodorant generating means (E'), deodorant selection means (F'), deodorant generation amount control means (D') and the like is connected as external connecting devices to the computer. If the item of "lovers" is specified, the smell of lovers imagined from a displayed mixing screen is searched according to the perfume classification table and as required, deodorant data classification table and as required, while generating deodorant. At this point of time, a guide button on the screen is specified to integrate the perfume retrieval information and as required, the deodorant retrieval information with the image/music synthesis information, so that necessary movie information is grabbed in and displayed in the form shown in FIG. 3. At this time, the movie software, perfume software and deodorant software exist in the same computer and the perfume software grabs information created with the deodorant software and movie software into its own system. Therefore, this perfume software can be constructed so as to be capable of executing programs corresponding to diversified movie software. That is, the perfume software can be provided with deodorant software and movie function or a marketed movie software can be installed in a computer capable of creating perfumes. If perfume retrieval information and depending on the case, deodorant retrieval information and image/music information are prepared, next processing is simulation work for creating an object information by gathering these pieces of information.

Figure 3:
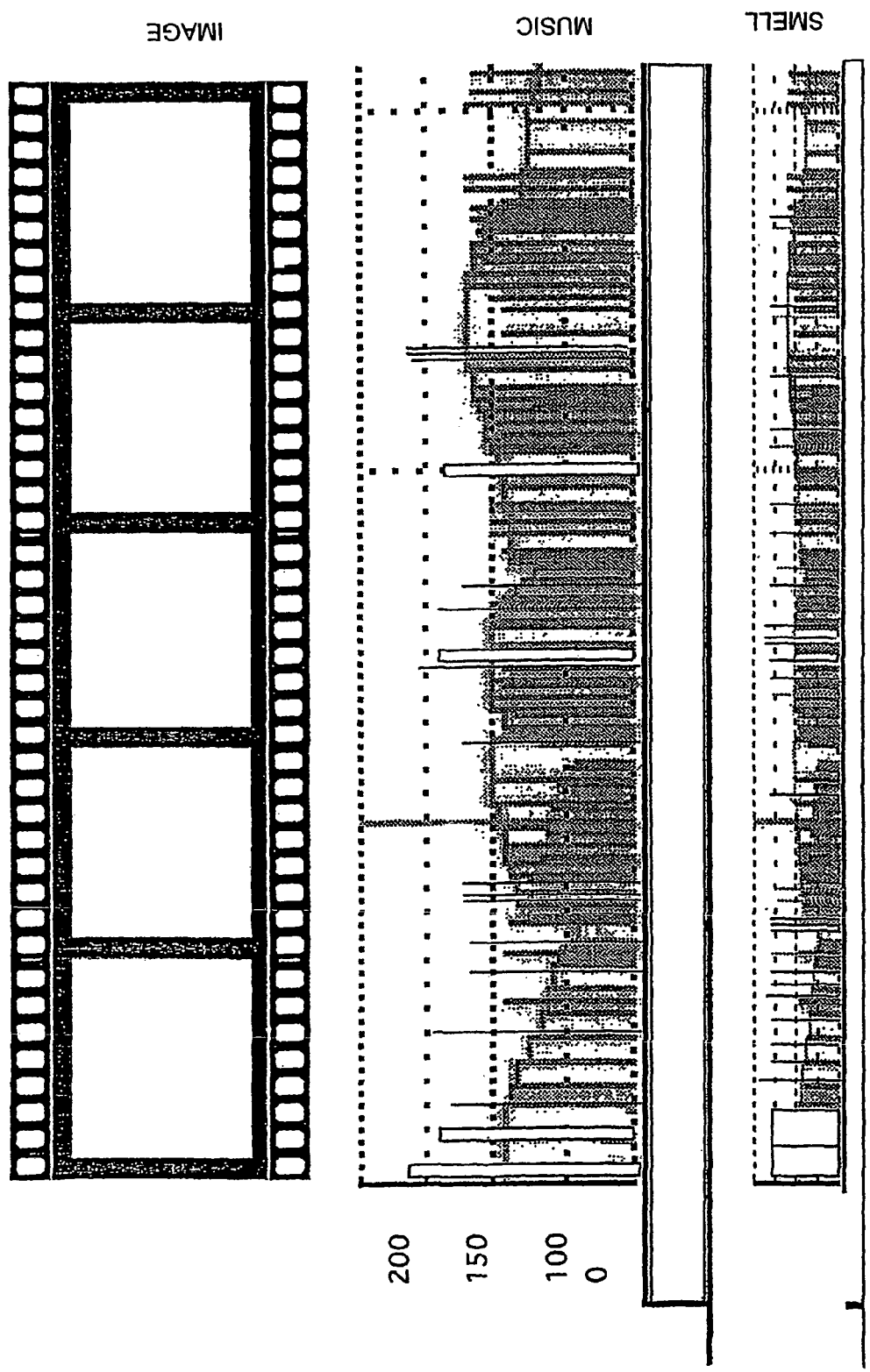
FIG. 3 is an enlarged diagram of portions indicating "image frame feeding", "sound wavelength" and "perfume wavelength" of FIG. 2.

The first stage of FIG. 3 shows image frames, and the second stage thereof shows sounds of musical instruments and people corresponding to each image, and the third stage shows a space for perfume which is to be arranged corresponding to each still image and sound image. With an image screen created by feeding image frames or animation images which are moved continuously and music information produced by a sound generation device connected to a computer, perfume data is displayed at the same time with the information. For example, the waveform of the lovers' perfume information is corrected and determined according to each object so as to most match this image and music, and then recorded. Because in this case, the perfume information is expressed by a plurality of kinds of perfume containing members, the amount of perfume discharged therefrom, and time passage consumed for it, the relation between a specific perfume containing member, the discharge amount and time needs to be stored. Thus, as for the perfume information, the perfume needs to be changed in various ways corresponding to a change in time like musical information. For example, if it is intended to change from a fresh smell to a sweet smell in accordance with changes in scene and music, in the case where there is a perfume A at the beginning of a first phrase, a perfume B is set up at the beginning of a second phrase, some changes are applied manually through the mixing screen or deodorant is employed at the same time, so that the perfume can be changed smoothly from the perfume A to the perfume B as a result of computer operation. Its information can be displayed, and stored in a memory temporarily or stored in a hard disc.

FIG. 1 shows a CPU and storage means. If a signal enters from outside, the CPU receives its instruction and starts up a control program stored in, for example, the memory so as to take out a perfume classification table and other perfume information's from a hard disc. Further, depending on the case, a deodorant classification table and deodorant information are taken out and an analysis processing program stored in the memory separately is started for computation and then, a result is introduced. This result is displayed on a screen through I/O control means, or driver software for driving a smell generating apparatus which is an external output execution program is executed through the I/O control means. The perfume software and deodorant software may be provided through a package like "Word" made by Microsoft. Then, this is installed in a marketed computer and usually stored in its hard disc. If the perfume software or deodorant software is installed in a computer, (A) a program for controlling the perfume system or deodorant system is automatically stored in the storage memory and (B) perfume data (perfume classification table and various perfume data) and deodorant data are automatically stored in the storage memory and hard disc. After a CPU 1 receives an execution instruction of driver software, the smell generating apparatus introduces information from a memory in which an execution procedure is stored and operates a driving section (oscillator, opening/closing valve, fan and the like) which is output means through the I/O control section 3.

Then, a person who takes pleasure in a smell prepares such medium as CDs, MOs, DVDs, magnetic tapes and the like containing images and sounds (including music) as required as well as smell information. On the other hand, the smell generating apparatus of the present invention is connected to an appropriate display unit like a cathode-ray tube and a sound generation device through a computer. In this case, the image display means and/or the sound generation device need to be provided with the function for fetching and reproducing such a medium as CD, MO, DVD, magnetic tape and the like. Likewise, the receiving/reproducing device on the side of the person who takes pleasure needs to be set to usable condition through a provided medium (CD, MO, DVD, magnetic tape and the like). If a CD, MO, DVD, magnetic tape or the like is grabbed into the image display means or sound generation means, information containing only perfume data or information containing perfume data and deodorant data is inserted, the information flows into the smell generating means or the deodorant generating means, so that a smell is generated. If image, sound and smell are stored as information in such a medium as the CD, MO, DVD, magnetic tape, and the like, the smell can be enjoyed with the image and music as required when the medium is set up and the device is started.

According to the present invention, data on images, data on music and data on combination of a smell and deodorant can be input to three tracks in parallel or input to a track alternately in fragments. In the former case, a reading device needs to have a capability of reading the three kinds of data separately while in the latter case, the reading device needs to have a capability of separating and reproducing the three different kinds of data.

According to the present invention, because the perfume and deodorant are formed into data, these may be used as analog information or as digital information. The digital information is a numerical signal and by using a gap between image or music information or inserting some information in parallel, images and music information can be used just as if they are transferred or transmitted. The signal information is stored in such a storage medium as hard disc, CD, DVD, magnetic tape and carried out and the memory medium is inserted into other computer, video recorder, a display machine, a display device, an acoustic appliance and if a smell generating apparatus can be mounted, that memory medium can be inserted therein so as to make use of the smell. Further, the signal perfume information or deodorant information is compressed by encryption and transmitted to other points using The Internet through communication line with a modem, terminal adaptor or the like. Alternatively, it can be stored and stored in provider's server. The perfume information or deodorant information is down-loaded from a network server through a computer or a television set connected to the Internet and uncompressed and decrypted by using specialized uncompression/decryption software preliminarily installed and then reproduced. Or when analog electric wave or digital signal containing perfume information is transmitted through a radio transmitter, receiving that signal by a portable phone, a television set or radio and having perfume re-use program, provided with a perfume generating device, the same perfume can be used. To reproduce information in a different apparatus or at a different place after transmitting it, the same smell generating apparatus, perfume containing member, or depending on cases, deodorant containing member controlled under numbers are required. Although the perfume exists as mixed information like images and music upon transmission or transfer of data, the perfume or deodorant as information can be transferred or transmitted independently each. For the information like this, the same apparatus can be provided with receiving function as well as transmitting function so as to cope with bi-directional communication. In bi-directional communication, if a computer at the other end does not have smell program software, that program is transmitted to the other party through computer and the other party can generate a specific smell using that received program if it is provided with the aforementioned (A), (A'), (F), (F').

Figure 9:
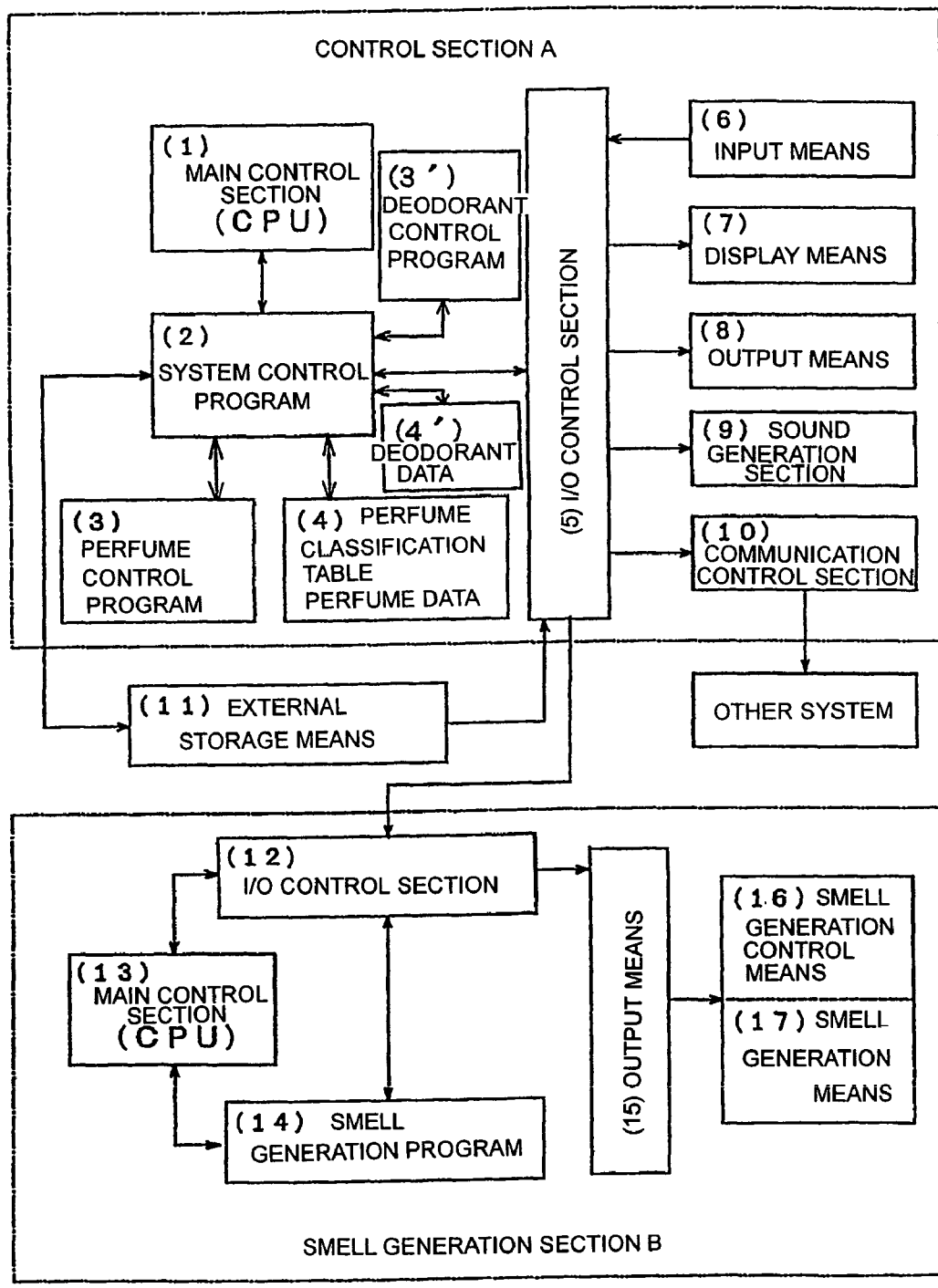
FIG. 9 is a flow sheet indicating an example of the smell generating system of the present invention.

The smell generating system of the present invention is divided roughly to a control section A and a smell generating section B as shown in FIG. 9. In FIG. 9, the item about the deodorant is omitted. The former is a portion for creating perfume information corresponding to a desired smell by computer control while the latter is a portion for generating an object smell using the perfume information. The control section A operates a system design program including the perfume control program (3), the deodorant control program (3'), the perfume classification table/perfume data (4), and deodorant classification table/deodorant data (4') under control by the CPU (1) and the system control program (2). That is, mixing operation for perfume selection and deodorant selection is enabled by starting the perfume control program (3) and the deodorant control program (3'). The perfume classification table and perfume data (4) and deodorant classification table and deodorant data (4') are read out and displayed on the display means (7), and perfume data and deodorant data are extracted by selective operation of the input means (6). A smell is generated at the smell generating section B using the extracted perfume data and deodorant data and if this generated smell is desired to be corrected, the perfume data and deodorant data are corrected, and the corrected perfume data and deodorant data are re-registered in the system control program (2) with the perfume data and deodorant data before change. This process is executed by operating successively according to an operation menu in the display means (7). As a result, smell generation control information including extracted (retrieved) or corrected simulation information can be sent out outside by a printing means (8), or music information which occurs upon simulation or mixing can be expressed outside (9) or transmitted to other medium through the communication control section (10). This information can be stored temporarily in a memory or external storage device (11). Next, the smell generating section B receives information transmitted through the I/O control section (5) of the control section A by means of its own I/O control section (12). The CPU (13) starts up the smell generation program (14) stored in a memory. The smell generation program (14) in the memory combines corresponding perfume or deodorant as required with information of the control section A and generates a signal corresponding to the generation amount or air feeding amount of the fan. Then, the output means (15) is started by the I/O control section (12) and electric signal is transmitted to the smell generation control means (16). The smell generation control means (16) starts up the smell generating means (17) based on a transmitted signal. In the meantime, the perfume control program (3) of the control section A can be used in place of the smell generation control means (16) and the smell generating means (17).

Embodiment 1

When a material which is an element of aromatotherapy is used with the smell generating apparatus together with a medium belonging to a genre called as environment video and environment music relaxes exhausted human body, relaxation effect can be intensified further.

Embodiment 2

A feeling of being present at a real scene can be intensified by generating a smell that befits a scene of a movie.

Embodiment 3

If a smell is generated by perfume software created based on a musician's image, corresponding to its melody, the artistic value is intensified. This can be achieved in a vehicle compartment as well as in a room, thereby contributing to relaxation of human mentality.

Embodiment 4

If the smell of curry is produced coincident with a scene of eating curry in a cooking TV program or a movie, a feeling of being present at that situation can be further intensified.

Embodiment 5

If the perfume generating means is connected to the other party's television set, smell can be transmitted to the other party by sending its perfume data through a video phone.

The address used for transmission/reception of the present invention is usually composed of numerals and/or alphabets. For example, two to four numerical letters are combined to specify the kind of a smell, a combination of smells, use amount of each perfume and the like. Further, a combination of perfume and deodorant, each use amount, discharge timing, emission duration time and the like are expressed with numerical letters and alphabet according to a specified rule, so that the transmission and reception are facilitated without any error.

Although the present invention will be described with reference to examples for carrying out the invention, the present invention is not limited thereto.

Example 1

An example of generating a smell which befits a scene in which lovers talk pleasantly with a matching music as a background will be described. Although the smell is indispensable in daily life, people rarely make up a desired smell and therefore, they can never create an object smell without any guideline except a specialist. Then, a basic prescription matching the image of lovers is produced by a specialist preliminarily and this is input into the perfume classification table.

Figure 7:
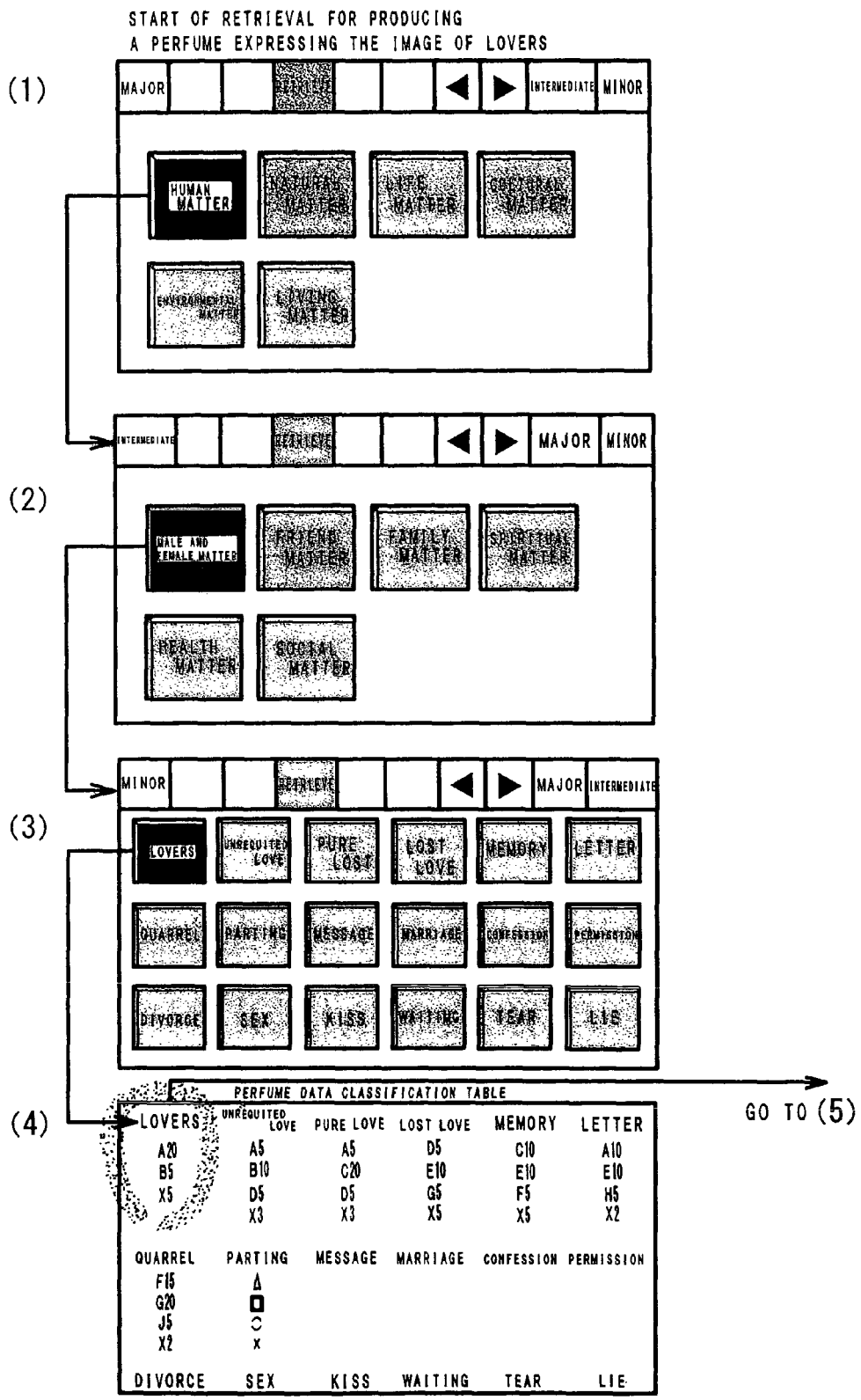
FIG. 7 shows changes of a display screen from a major classification table to a classification table indicating perfume data related to lover.
Figure 8:
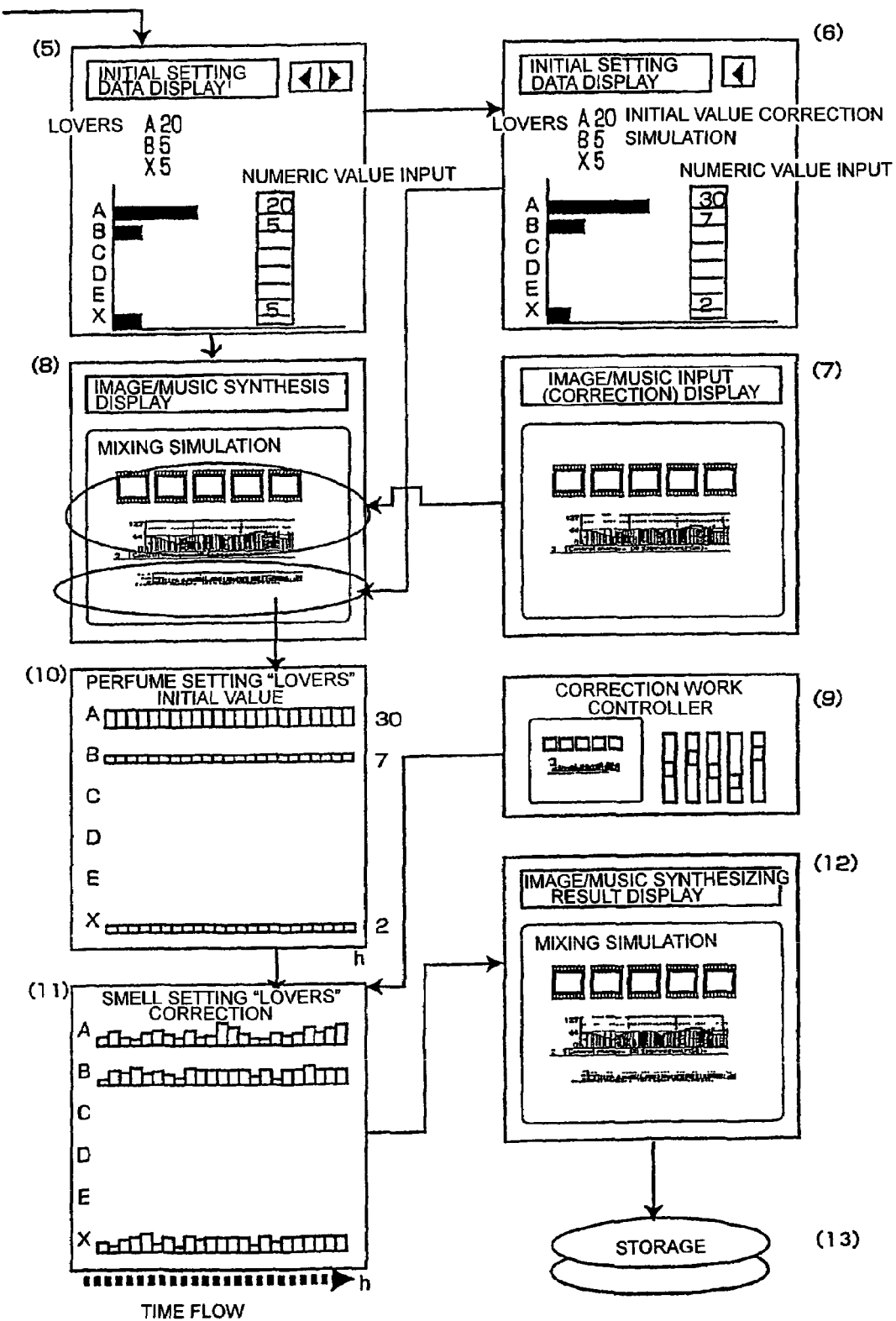
FIG. 8 shows development of the display screen for processing subsequent to the perfume data classification table about lover of FIG. 7.

The perfume software in the computer is activated and as shown in FIG. 7, the item of human matter in the major classification table is clicked so as to display the intermediate classification table on the screen. By clicking the item of male and female matter in the intermediate classification table, the minor classification table of low level concept is displayed on the screen. If the item of lovers in the intermediate classification table is clicked, the data classification table of the lovers matter is displayed on the screen. Then, if the item of lovers is clicked, the screen shown in FIG. 8(5) is displayed. Numeral A indicates the component contained in the perfume container A, Numeral B indicates the component contained in the perfume container B, and Numeral X means that the fan shown in FIG. 1 is driven. Numerals 20 and 5 corresponding to A and B respectively as shown in FIG. 8(5) mean indices for indicating the generation amounts of the perfumes of the components A, B, and number 5 of numeral X indicates the air feeding strength of the fan. The smell generating apparatus shown in FIG. 1 is driven to generate a ready-made smell based on the image of lovers according to the aforementioned prescription and that smell is sensed. If this smell is acceptable, the synthesizing work for synthesizing an image, sound with the smell shown in FIG. 8(8) is started. If it is desired to correct the ready-made smell of the item of lovers, the simulation processing shown in FIG. 8(6) is carried out. In FIG. 8(6), the component A, the component B and numeral X are changed to 30, 7, and 2 respectively, by generating the smell and an initial value is set up and registered in the computer.

Subsequently, movie data in which the image and music of a scene of lovers shown in FIG. 8(7) talking with each other are synthesized, is input to a computer which the person is currently operating from an outside device. However, this input work does not always have to be carried out at this point of time, but may be executed at any time before this time. Next, the image and music are grabbed into the perfume software.

Consequently, the initial setting data of (5) or the initial correction data of (6) is displayed on the synthesis screen of (8). At this stage, the synthetic data of the image and music is integrated with the perfume setting data on the screen. At the stage of the synthesizing screen of (8), its top line indicates image data frame feeding screen, the middle line indicates music data frame feeding screen and the bottom line indicates perfume data frame feeding screen. The image data and music data have been already corrected at this stage. If there is still a capability for correcting the image and music data on this software, they may be corrected. By interlocking the movie data with the perfume data, mixing work for changing the perfume data in various ways over time is carried out.

The perfume data before the mixing work is started is balanced against a time passage with its initial setting data (A=30, B=7, X=2) as shown in FIG. 8(10). That is, a perfume once determined continues to be expressed on the same level.

Next, a processing for changing the perfume over time based on this screen is started. Using the correction work control screen (9) shown in FIG. 8 attached to the perfume software, first, changes of image and music over time are displayed so as to recognize the continuous changes. Second, the stream of image and music is stopped (fixed) temporarily at a start position of image and music. Third, the perfume data on the bottom line of FIG. 8(8) is changed over time with respect to the stopped image and music displayed data. If explaining this operation, a time scale like a gauge is set up from the left to the right corresponding to the fixed change with time sequence display screen of image and music. Its numeric value is changed by inputting a value into each scale or moving a scale level gauge by using a mouse pointer. For example, perfume numeric values located at a position after 10 seconds are changed in the direction from the left to the right from its initial value of A=30, B=7, X=2 to A=10, B=10, X=3 and next, A=20, B=30, X=5 is input as perfume numeric values at a position after 20 seconds. The perfume data is created by continuing such a work so as to link image and music data with perfume data. To link the image and music data with perfume data, it is preferable to synchronize the perfume data with a timing of image and music changes. This perfume data has the same characteristic as waveform processing of the music data and is prepared at a timing synchronous with the music data. Because such a processing is achieved on a single screen, a display image about image and music is stopped (fixed) just before that display image is changed to a next phrase beyond a range in which they can be expressed and then corrected. After repeating this processing, a final result is obtained. When this final result is settled, data of (12) is stored in a recording medium such as a hard disc (13).

INDUSTRIAL APPLICABILITY (1) The present invention enables a non-specialist to generate a desired smell relatively easily.
(2) The remedial treatment by aromatotherapy can be further simplified.
(3) An artistic world or a dreamy world joined with an image world or an acoustic world can be achieved.
(4) If both parties possess the apparatus of the present invention, respectively, as the apparatuses are executed and operated based on electric signals, the smell can be transmitted or received by communication.

The invention claimed is:

1. A smell generating apparatus for generating a desired smell under computer control, comprising:
 perfume information that sets preliminarily kinds of perfumes constituting a smell, its generation amount and variation with time of the generation amount;
 a smell generation program;
 storage means for storing the smell generation program;
 smell generation control means for controlling smell generation according to the smell generation program and the perfume information;
 smell selecting means for selecting a specific perfume containing member from perfume containing members under control by the smell generation control means;
 smell generating means for generating the smell from the specific perfume containing member, by rotating or vibrating a porous container member containing the perfume with a shape memory alloy, based on the smell selecting means;
 smell classification table memory means for storing a smell classification table comprising a plurality of smell items defining the perfume information, the perfume information including a combination of perfumes constituting a smell of a smell item, a generation amount of the smell and variation with time of the generation amount;
 perfume information registration means for registering the perfume information;
 perfume information selecting and extracting means for selecting a predetermined smell item from the smell classification table and extracting corrected perfume information corresponding to the predetermined smell item;
  association means for associating at least one of continuous images and sounds with the selected smell item; and
 at least one of image reproducing means and sound generating means for outputting the associated at least one of continuous images and sounds,
 wherein the desired smell is generated along with an output of the associated at least one of continuous images and sounds based on the perfume information corresponding to the predetermined smell item of the smell classification table or the corrected perfume information thereof.

2. The smell generating apparatus according to claim 1, further comprising deodorant generating means for generating deodorant at the same and/or a predetermined interval when the smell is generated.

3. The smell generating apparatus according to claim 1, wherein a porous container member containing the perfume is in a shape of a propeller and the smell generating means forms a part of a motor shaft for discharging perfume so that the smell generating means generates a smell.

4. The smell generating apparatus according to claim 1, wherein the smell generating means generates a smell by providing a container member coated or impregnated with a perfume on a rotating body.

5. The smell generating apparatus according to claim 1, wherein the smell generating means generates a smell by heating, vibrating or rubbing a porous container member containing the perfume.

6. The smell generating apparatus according to claim 1, wherein the smell generating means generates a smell by applying a pressure to a porous container member, or a liquid, semi-liquid or gas container member containing the perfume.

7. The smell generating apparatus according to claim 1, wherein the smell generating means generates a smell by applying an ultrasonic vibration to a liquid container member containing the perfume.

8. The smell generating apparatus according to claim 1, further comprising communication means for transmitting and receiving the perfume information to and from another smell generating apparatus.

9. The smell generating apparatus according to claim 1, further comprising:
 a deodorant control program;
 deodorant data operated under computer control;
 deodorant selecting and generating means for selecting and generating a specific deodorant; and
 deodorant generating control means for controlling deodorant generation.

10. The smell generation apparatus according to claim 1, wherein the smell classification table comprises a plurality of smell classification tables selected according to the perfume information.

11. A smell generation method for generating a desired smell under computer control, comprising:
 providing:
  perfume information that sets preliminarily kinds of perfumes consisting a smell, its generation amount and variation with time of the generation amount,
  a smell generation program,
  storage means for storing the smell generation program, and
  smell generation control means for generating the smell and controlling smell generation according to the smell generation program and the perfume information;
 selecting a specific perfume containing member from perfume containing members under control by the smell generation control means;
 generating the smell from the specific perfume containing member, by rotating or vibrating a porous container member containing the perfume with a shape memory alloy, based on the smell selecting means;
 storing the perfume information in a smell classification table memory means, as a smell classification table comprising a plurality of smell items that correspond to respective perfume information, the respective perfume information consisting of kinds of perfumes constituting the smell, the generation amount of the smell and variation with time of the generation amount;
 registering the perfume information in a perfume information registration means;
 selecting a predetermined smell item from the smell classification table and extracting corrected perfume information corresponding to the predetermined smell item; and
 generating the desired smell based on the perfume information corresponding to the predetermined smell item of the smell classification table or the corrected perfume information thereof; and
 associating the desired smell with at least one of continuous images and sounds, wherein the desired smell is generated along with an output of the associated at least one of continuous images and sounds.

12. The smell generation method according to claim 11, wherein the classification means is a classification table in which the image corresponds to the smell.

13. The smell generation method according to claim 11, wherein the classification means is a means in which an image corresponds to a smell based on a tree structure.

14. The smell generation method according to claim 11, wherein the smell is displayed on the display apparatus as a wave form corresponding to an axis of time and emission amount, and smell discharging timing, emission duration and emission amount are controlled by correcting the wave form.

15. The smell generation method according to of claim 11, wherein a deodorant is discharged at least one of at the same time and at a predetermined interval when the smell is generated.

16. The smell generation method according to claim 11, further comprising providing a communication means for transmitting and receiving the perfume information to and from a smell generating apparatus.

17. The smell generation method according to claim 16, wherein an address is provided to the perfume information, the address is transmitted through the communication means, and a smell corresponding to the address is generated on the reception side.

18. The smell generation method according to claim 16, wherein the perfume information is compressed and transmitted through the communication means, and the perfume information is uncompressed and decrypted with specialized uncompression/decryption software.

19. The smell generation method according to claim 11, further providing:
 a deodorant control program;
 deodorant data operated under computer control;
 deodorant selecting and generating means for selecting and generating a specific deodorant; and
 deodorant generating control means for controlling deodorant generation.

20. The smell generation method according to claim 11, wherein the smell classification table comprises a plurality of smell classification tables selected according to the perfume information.

* * * * *